(12) United States Patent
Flood

(10) Patent No.: US 12,364,723 B2
(45) Date of Patent: Jul. 22, 2025

(54) THERMOSTABLE COMPOSITIONS COMPRISING LIVE ATTENUATED HERPES SIMPLEX VIRUS TYPE 1

(71) Applicant: AMGEN INC., Thousand Oaks, CA (US)

(72) Inventor: Enrique Alexander Flood, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 864 days.

(21) Appl. No.: 17/417,893

(22) PCT Filed: Dec. 27, 2019

(86) PCT No.: PCT/US2019/068700
§ 371 (c)(1),
(2) Date: Jun. 24, 2021

(87) PCT Pub. No.: WO2020/140012
PCT Pub. Date: Jul. 2, 2020

(65) Prior Publication Data
US 2022/0193161 A1 Jun. 23, 2022

Related U.S. Application Data

(60) Provisional application No. 62/785,307, filed on Dec. 27, 2018.

(51) Int. Cl.
| | | |
|---|---|---|
| *A61K 35/763* | (2015.01) | |
| *A61K 9/19* | (2006.01) | |
| *A61K 47/26* | (2006.01) | |
| *A61K 47/42* | (2017.01) | |
| *C12N 7/00* | (2006.01) | |

(52) U.S. Cl.
CPC .............. *A61K 35/763* (2013.01); *A61K 9/19* (2013.01); *A61K 47/26* (2013.01); *A61K 47/42* (2013.01); *C12N 7/00* (2013.01); *C12N 2710/16632* (2013.01)

(58) Field of Classification Search
CPC ........ A61K 35/763; C12N 2710/16632; C12N 2710/16621; C12N 2710/16643
See application file for complete search history.

(56) References Cited

U.S. PATENT DOCUMENTS

| | | |
|---|---|---|
| 4,337,242 A | 6/1982 | Markus |
| 4,985,244 A | 1/1991 | Makino |
| 5,024,836 A | 6/1991 | Mcaleer |
| 5,811,097 A | 9/1998 | Allison |
| 5,824,318 A | 10/1998 | Mohr |
| 5,855,887 A | 1/1999 | Allison |
| 6,051,227 A | 4/2000 | Allison |
| 6,207,157 B1 | 3/2001 | Gu |
| 6,682,736 B1 | 1/2004 | Hanson |
| 6,764,675 B1 | 7/2004 | Whitley |
| 6,770,274 B1 | 8/2004 | Martuza |
| 6,984,720 B1 | 1/2006 | Korman |
| 7,063,835 B2 | 6/2006 | Coffin |
| 7,168,757 B2 | 1/2007 | Futatsuhashi |
| 7,223,593 B2 | 5/2007 | Coffin |
| 7,488,802 B2 | 2/2009 | Collins |
| 7,605,238 B2 | 10/2009 | Korman |
| 7,744,899 B2 | 6/2010 | Whitley |
| 7,749,745 B2 | 7/2010 | Johnson |
| 7,943,743 B2 | 5/2011 | Korman |
| 8,008,449 B2 | 8/2011 | Korman |
| 8,084,039 B2 | 12/2011 | Stinchcomb |
| 8,217,149 B2 | 7/2012 | Irving |
| 8,273,568 B2 | 9/2012 | Martuza |
| 8,420,071 B2 | 4/2013 | Whitley |
| 8,470,577 B2 | 6/2013 | Johnson |
| 10,034,938 B2 | 7/2018 | Vanderwalde |
| 2005/0164910 A1 | 7/2005 | Sakai |
| 2006/0141483 A1 | 6/2006 | Calton |
| 2008/0248551 A1 | 10/2008 | Stinchcomb |
| 2011/0243988 A1 | 10/2011 | Ohtake |
| 2013/0202639 A1 | 8/2013 | Kousoulas |
| 2015/0150964 A1 | 6/2015 | Anderson |

FOREIGN PATENT DOCUMENTS

| | | |
|---|---|---|
| CN | 101926990 A | 12/2010 |
| JP | S577423 A | 1/1982 |
| JP | 2643982 B2 | 8/1997 |
| WO | 199600007 | 1/1996 |

(Continued)

OTHER PUBLICATIONS

Cassady et al., "Herpesvirus Vectors for Therapy of Brain Tumors," Open Virol. J. 4:103-108 (2010).
Essbauer, et al., Long-lasting stability of vaccinia virus (orthopoxvirus) in food and environmental samples, Zoonoses Public Health. 2007;54(3-4):118-24. doi: 10.1111/j.1863-2378.2007.01035.x.
Hansen L, et al., Freeze-drying of live virus vaccines: A review, (2015) Freeze-Drying of Live Virus Vaccines: A Review. Vaccine 33:5507-5519.
JP 2021-537096 Office Action (Nov. 10, 2023).
Liu, et al., ICP34.5 deleted herpes simplex virus with enhanced oncolytic, immune stimulating, and anti-tumour properties, Gene Ther. Feb. 2003; 10(4):292-303. doi: 10.1038/sj.gt.3301885.
Liu, et al., Preclinical evaluation of herpes simplex virus armed with granulocyte-macrophage colony-stimulating factor in pancreatic carcinoma, Journal List World J Gastroenterol v.19(31); Aug. 21, 2013 PMC3746387.

(Continued)

*Primary Examiner* — Jeffrey S Parkin
(74) *Attorney, Agent, or Firm* — Melissa E. Karabinis

(57) ABSTRACT

Provided herein is a powder comprising a live, attenuated virus, recombinant human serum albumin (rHSA), a sugar other than lactose, a sugar alcohol, a source of phosphate, a source of chloride, wherein the composition is substantially free of lactose, gelatin, antibiotic, and free amino acids. In exemplary aspects, the powder is a lyophilizate of a liquid composition. Related liquid compositions, methods of preparing an oncolytic virus for administration and methods of treating melanoma are also provided herein.

20 Claims, 5 Drawing Sheets

(56) References Cited

FOREIGN PATENT DOCUMENTS

| | | |
|---|---|---|
| WO | 199639841 | 12/1996 |
| WO | 199907394 | 2/1999 |
| WO | 99/12568 A1 | 3/1999 |
| WO | 1999/012568 | 3/1999 |
| WO | WO 99/12568 * | 3/1999 |
| WO | 1999/055348 | 11/1999 |
| WO | 1999/062500 | 12/1999 |
| WO | 2000054795 A1 | 9/2000 |
| WO | 2003042402 A2 | 5/2003 |
| WO | 2003/082200 | 10/2003 |
| WO | 2005/004795 | 1/2005 |
| WO | 2006002394 A2 | 1/2006 |
| WO | 2007/132480 | 11/2007 |
| WO | 2008156712 A1 | 12/2008 |
| WO | 2009/014774 | 1/2009 |
| WO | 2010036959 A2 | 4/2010 |
| WO | 2010089411 A2 | 8/2010 |
| WO | 2011/032108 | 3/2011 |
| WO | 2011066342 A2 | 6/2011 |
| WO | 2011082400 A2 | 7/2011 |
| WO | 2011/119925 | 9/2011 |
| WO | 2011/159877 | 12/2011 |
| WO | 2011161699 A2 | 12/2011 |
| WO | 2013006795 A2 | 1/2013 |
| WO | 2013/106398 | 7/2013 |
| WO | 2013/177172 | 11/2013 |
| WO | 2014036412 | 3/2014 |
| WO | WO 2016/100364 A1 * | 6/2016 |
| WO | 2017118864 A1 | 7/2017 |
| WO | 2017118865 A1 | 7/2017 |
| WO | 2017118866 A1 | 7/2017 |
| WO | 2017118867 A1 | 7/2017 |
| WO | 2017181420 A1 | 10/2017 |
| WO | 2018006005 A1 | 1/2018 |
| WO | 2018026872 A1 | 2/2018 |
| WO | 2018127713 A1 | 7/2018 |
| WO | 2020140012 | 7/2020 |

OTHER PUBLICATIONS

Meignier et al., "In vivo behavior of genetically engineered herpes simplex viruses R7017 and R7020: construction and evaluation in rodents", J Infect Dis., vol. 158 (3), pp. 602-614 (1988).

Mineta, et al., Attenuated multi-mutated herpes simplex virus-1 for the treatment of malignant gliomas, Nat Med., Sep. 1995;1(9):938-43. doi: 10.1038/nm 995-938.

Rheinbaben, et al., Environmental resistance, disinfection, and sterilization of poxviruses, (2007) Long-Lasting Stability of Vaccinia Virus (Orthopoxvirus) in Food and Environmental Samples. Zoonoses and Public Health 118-124 54.

Roy et al., Troubleshooting During the Manufacture of Lyophilized Drug Product-Begin Prepared for the Unexpected, Am Pharm Rev (2012).

Thompson et al., "DNA Sequence and RNA Transcription through a Site of Recombination in a Non-neurovirulent Herpes Simplex Virus Intertypic Recombinant", Virus Genes, vol. 1 (3), pp. 275-286 (1988).

Todo et al., "Oncolytic herpes simplex virus vector with enhanced MHC class I presentation and tumor cell killing", Proc Natl Acad Sci USA, vol. 98 (11), pp. 6396-6401 (2001).

Varghese et al., "Oncolytic herpes simplex virus vectors for cancer virotherapy," Cancer Gene Ther. 9:967-978 (2002).

White, et al., Development of a stable liquid formulation of live attenuated influenza vaccine, Vaccine 34 (2016) 3676-3683.

Yannarell et al., Stabilizing cold-adapted influenza virus vaccine under various storage conditions, J Virol Methods 102 (1-2): 15-25 (2002).

Patent Cooperation Treaty application No. PCT/US2019/0687001 International Search Report, completed Mar. 11, 2020, 3 pages.

Berard A, Coombs KM (2009) Mammalian reoviruses: propagation, quantification, and storage. Current protocols in microbiology: 15C-1.

Burger et al., "Stabilizing Formulations for Inhalable Powders of Live-Attenuated Measles Virus Vaccine," Journal of Aerosol Medicine and Pulmonary Drug Delivery 21(1): 25-34 (2008).

CDC Media Statement on Newly Discovered Smallpox Specimens (n.d.). Available: http://www.cdc.gov/media/releases/2014/s0708-NIH.html.

Complete List of Vaccines Licensed for Immunization and Distribution in the US (n.d.). Available: http://www.fda.gov/BiologicsBloodVaccines/Vaccines/ApprovedProducts/ucm093833.htm. Date accessed Oct. 2, 2017.

Condit RC, Moussatche N, Traktman P (2006) In a nutshell: structure and assembly of the vaccinia virion. Advances in virus research 66: 31-124.

Evans RK, Nawrocki DK, Isopi LA, Williams DM, Casimiro DR, et al. (2004) Development of stable liquid formulations for adenovirus-based vaccines. J Pharm Sci 93: 2458-2475.

FDA found more than smallpox vials in storage room (n.d.). Available: https://www.washingtonpost.com/national/health-science/fda-found-more-than-smallpoxvials- in-storage-room/2014/07/16/850d4b12-0d22-11e4-8341-b8072b1e7348_story.html.

Ghobadloo et al., "Carbohydrate-Based Ice Recrystallization Inhibitors Increase Infectivity and Thermostability of Viral Vectors", Scientific Reports, vol. 4, Jan. 1, 2014 (Jan. 1, 2014), pp. 5903-5903, XP055254002, GB ISSN: 2045-2322, DOI: 10.1 038/srep05903.

Kueltzo LA, Wang W, Randolph TW, Carpenter JF (2008) Effects of solution conditions, processing parameters, and container materials on aggregation of a monoclonal antibody during freeze-thawing. J Pharm Sci 97: 1801-1812.

Maclean et al., (1991) Journal of General Virology 79: 631-639.

McCollum AM, Li Y, Wilkins K, Karem KL, Davidson WB, et al. (2014) Poxvirus 25 viability and signatures in historical relics. Emerging infectious diseases 20: 177.

Medicago (http://www.medicago.se/sites/default/files/pdf/productsheets/PBS_Buffer_v._01.pdf (2010) (Year: 2010).

Mettenleiter TC (2002) Herpesvirus assembly and egress. Journal of virology 76: 1537-1547.

Mohr & Gluzman (1996) EMBO 15:4759-4766.

Mulvey et al. (1999) J Virology, 73:4, 3375-3385.

Roizman B (1982) The Family Herpesviridae: General Description, taxonomy and classification. The Viruses, vol. A, Herpesviruses. New York: Plenum Press.

Russell et al., "Oncolytic virotherapy," Nature Biotechnology 30(7):658-670 (2012).

Shen and Nemunaitis, "Herpes simplex virus 1 (HSV-1) for cancer treatment," Cancer Gene Therapy 13(11):975-992 (2006).

Shire SJ (2009) Formulation and manufacturability of biologics. Current opinion in biotechnology 20: 708-714.

Sokhey J, Gupta CK, Sharma B, Singh H (1988) Stability of oral polio vaccine at different temperatures. Vaccine 6: 12-13.

Vaccine Ingredients and Manufacturer Information, https://web.archive.org/web/20141112183109/https://vaccines.procon.org/view.resource.php?resourceID=005206, Nov. 12, 2014.

Varshney and Singh, Editors, "Lyophilized Biologics and Vaccines," © Springer Science+Business Media, New York 2015.

Wang et al., "Anti-tumor effect of oncolytic herpes simplex virus G47delta on human nasopharyngeal carcinoma," Chinese Journal of Cancer 30(12):831-841 (2011).

* cited by examiner

THERMOSTABLE COMPOSITIONS COMPRISING LIVE ATTENUATED HERPES SIMPLEX VIRUS TYPE 1

CROSS REFERENCE TO RELATED APPLICATIONS

This application is a national stage application under 35 U.S.C. § 371 of International Application No. PCT/US2019/068700, having an international filing date of Dec. 27, 2019; which claims the benefit under 35 U.S.C. 119(e) of U.S. Provisional Application No. 62/785,307, filed Dec. 27, 2018, the entire contents of which are incorporated herein by reference.

BACKGROUND

Live viruses, such as herpes simplex virus, are typically unstable for extended periods of time at storage temperatures higher than −80° C. Lack of thermo-stability poses a challenge for such viruses, particularly for therapeutic viruses in a liquid formulation. Such therapeutic virus compositions must be stored and transported frozen and used soon after thawing to maintain their therapeutically effective infectivity.

The lack of thermo-stability poses operational challenges that increase the cost of manufacture, storage and transportation. During manufacturing operations, for example, freeze/thaw cycles could lead to sub-optimal process yields and lack of necessary flexibility in the supply chain. Storage and transportation are also challenging resulting in complicated handling and complex supply chains.

The lack of thermo-stability also poses commercial challenges. Live virus compositions that require −80° C. storage to insure stable shelf life lead to complex storage and handling protocols for health care providers. Such limitations increase the risk of product loss (e.g., due to mishandling) and product waste (e.g., the entire product is not used after thawing). This has the potential to increase cost to the customer.

Lyophilization is a freeze-drying process that removes water from a drug product after it is frozen and placed under a vacuum. During this process, water sublimes changing from ice to vapor without passing through the liquid phase. Lyophilization is widely used for improving the stability of pharmaceuticals and biopharmaceuticals, including those comprising chemical APIs, peptides, oligonucleotides, and proteins (e.g., collagens, enzymes and antibodies), ultimately for the purpose of enhancing storage stability and lengthening shelf like. This process is not without its challenges however. Lyophilization can lead to delayed release of the drug product and rejection of drug product lots (Roy et al., Troubleshooting During the Manufacture of Lyophilized Drug Product-Begin Prepared for the Unexpected, Am Pharm Rev (2012) available at www.americanpharmaceuticalreview.com/Featured-Articles/126958-Troubleshooting-During-the-Manufacture-of-Lyophilized-Drug-Product-Being-Prepared-for-the-Unexpected/). In the context of viral formulations, the lyophilization process can damage the virus leading to low amounts of active virus upon reconstitution (Hansen L, Daoussi R, Vervaet C, Remon J-P, De Beer T (2015) Freeze-drying of live virus vaccines: A review. Vaccine 33:5507-5519). Also, the U.S. Food and Drug Administration notes that some of the disadvantages of lyophilization include increased handling and processing times, need for sterile diluents for reconstitution, and requirement for costly and/or complex equipment.

SUMMARY

The present disclosure provides a live virus formulation or composition that can be lyophilized to produce a stable lyophilized virus product allowing for storage at cold and ambient temperatures. The lyophilized product or powder is also provided herein. Without being bound to any particular theory, the presently disclosed formulations, products and powders reduce the constraints during manufacture, transportation, storage and use of the virus, by providing flexibility while mitigating the loss of viral stability and/or infectivity. The compositions of the present disclosure also prevent or minimize inactivation of the virus. The ability to handle, store, and transport a drug product or intermediate product without loss of potency (or activity) is of tremendous value because it allows for flexibility in the manufacturing process design, labeling, packaging operations, supply chain distribution of the final product, and health care provider handling.

Accordingly, the present disclosure provides a liquid composition comprising a live, attenuated virus, human serum albumin (e.g., recombinant human serum albumin "rHSA"), a sugar other than lactose, a sugar alcohol, a source of phosphate, and a source of chloride. In exemplary aspects, the liquid composition comprises greater than about 5 mg/mL and less than about 25 mg/mL rHSA, optionally, greater than about 10 mg/mL and less than about 25 mg/mL rHSA. In various aspects, the liquid composition comprises greater than about 15 mg/mL and less than about 25 mg/mL rHSA, optionally, wherein the liquid composition comprises about 17.5 mg/mL to about 22.5 mg/mL rHSA, optionally, about 20 mg/mL±2 mg/mL rHSA. In various aspects, the sugar of the liquid composition is sucrose and optionally the liquid composition comprises less than about 15 mg/mL sucrose, less than about 10 mg/mL sucrose or less than about 5 mg/mL sucrose. In various aspects, the liquid composition comprises less than about 3.8 mg/mL±0.38 mg/mL sucrose. In various instances, the sugar alcohol of the liquid composition is sorbitol and optionally the liquid composition comprises greater than about 10 mg/mL mg sorbitol and less than about 50 mg/mL sorbitol, optionally, greater than about 20 mg/mL mg sorbitol and less than about 40 mg/mL sorbitol. In some aspects, the liquid composition comprises less than about 45 mg/mL sorbitol, less than about 40 mg/mL sorbitol, less than about 35 mg/mL sorbitol, or about 26 mg to about 32 mg/mL sorbitol. In some aspects, the source of phosphate present in the liquid composition is potassium phosphate. In various instances, the liquid composition comprises greater than about 5 mg/mL and less than about 45 mg/mL potassium phosphate, optionally, less than about 40 mg/mL potassium phosphate (e.g., less than about 30 mg/mL potassium phosphate, less than about 20 mg/mL potassium phosphate), or about 13.5 mg to about 16 mg/mL potassium phosphate. In some instances, the source of chloride of the liquid composition is sodium chloride, and, optionally, is present in an amount greater than about 1 mg/mL and less than about 20 mg/mL sodium chloride. In some aspects, the liquid composition comprises less than about 15 mg/mL sodium chloride or less than about 10 mg/mL sodium chloride, e.g., about 3 mg to about 7 mg/mL sodium chloride. In exemplary instances, the composition is substantially free of lactose, gelatin, antibiotics, and free amino acids. In various aspects, the liquid composition consists essentially of or consists of: the live, attenuated virus, rHSA, sucrose, sorbitol, potassium phosphate, and sodium chloride. The liquid composition in some aspect has a pH of about 7.2 to about 7.6, optionally, a pH of about 7.4. In various aspects, the liquid composition has an osmolality less than about 700 mOsm/kg, optionally, less than bout 650 mOsm/kg (e.g., an osmolality less than about 600 mOsm/kg, optionally, about 525 mOsm/kg to about 575 mOsm/kg). In certain aspects, the liquid composition comprises not more than about 0.01 mM of any of lactose, gelatin, antibiotic, and free amino acids, optionally, not more than about 0.001 mM any of lactose, gelatin, antibiotic, and free amino acids.

In some embodiments, the live, attenuated virus is a herpes simplex virus (HSV), optionally, a herpes simplex virus 1 (HSV-1) strain. In various instances, the HSV-1 strain is selected from the group consisting of strain JS1, strain 17+, strain F, and strain KOS. In one embodiment, the HSV-1 is talimogene laherparepvec. In various instances, when the liquid composition is lyophilized and reconstituted with water to produce a reconstituted product, the potency of the live, attenuated virus in the reconstituted product is at least or about 30% of the potency of the live, attenuated virus before the liquid composition is lyophilized, optionally, at least or about 35% of the potency of the live, attenuated virus before the liquid composition is lyophilized. In some aspects, the liquid composition is lyophilized then reconstituted with water to produce a reconstituted product, the potency of the live, attenuated virus in the reconstituted product is at least or about 30% of the potency of the live, attenuated virus before the liquid composition is lyophilized, optionally, at least or about 40% of the potency of the live, attenuated virus before the liquid composition is lyophilized.

Also provided herein is a liquid composition comprising a live, attenuated HSV-1 (e.g., talimogene laherparepvec), about 18 mg/mL to about 22 mg/mL human serum albumin (e.g., rHSA), about 3.4 mg/mL to about 4.2 mg/mL sucrose, about 26 mg/mL to about 31.9 mg/mL sorbitol, about 13 mg/mL to about 16 mg/mL potassium phosphate, and about 5.1 mg/mL to about 6.3 mg/mL sodium chloride. Further provided is a liquid composition comprising a live, attenuated HSV-1 (e.g., talimogene laherparepvec), about 1.0% to about 3.0% (w/v) human serum albumin (e.g., rHSA), about 0.25% to about 0.45% (w/v) sucrose, about 2.0% to about 4.0% (w/v) sorbitol, about 60 mM to about 100 mM potassium phosphate, and about 80 to about 110 mM sodium chloride.

A product produced by lyophilizing or freeze-drying any one of the presently disclosed liquid compositions is further provided herein.

The present disclosure provides a powder produced by a method comprising removing water (e.g., via lyophilization) from a composition comprising a live, attenuated virus (e.g., HSV-1, optionally talimogene laherparepvec), recombinant human serum albumin (rHSA), a sugar other than lactose, a sugar alcohol, a source of phosphate, a source of chloride, wherein the composition is substantially free of lactose, gelatin, antibiotic, and free amino acids. Optionally, the composition from which water is removed (e.g., via lyophilization) comprises a live, attenuated HSV-1 (e.g., talimogene laherparepvec), about 18 mg/mL to about 22 mg/mL human serum albumin (e.g., rHSA), about 3.4 mg/mL to about 4.2 mg/mL sucrose, about 26 mg/mL to about 31.9 mg/mL sorbitol, about 13 mg/mL to about 16 mg/mL potassium phosphate, and about 5.1 mg/mL to about 6.3 mg/mL sodium chloride. Further provided is a powder produced by a method comprising removing water (e.g., via lyophilization) from a composition comprising a live, attenuated HSV-1 (e.g., talimogene laherparepvec), about 1.0% to about 3.0% (w/v) human serum albumin (e.g., rHSA), about 0.25% to about 0.45% (w/v) sucrose, about 2.0% to about 4.0% (w/v) sorbitol, about 60 mM to about 100 mM potassium phosphate, and about 80 to about 110 mM sodium chloride.

Additionally provided is a powder produced by a method comprising removing water from a composition comprising a live, attenuated HSV-1, about 18 mg/mL to about 22 mg/mL recombinant human serum albumin (rHSA), about 3.4 mg/mL to about 4.2 mg/mL sucrose, about 26 mg/mL to about 31.9 mg/mL sorbitol, about 13 mg/mL to about 16 mg/mL potassium phosphate, and about 5.1 mg/mL to about 6.3 mg/mL sodium chloride. In some aspects, the composition is frozen to obtain a composition comprising ice prior to removing water, and, optionally, the method further comprises placing the composition under a vacuum to remove the water (e.g., via lyophilization). In certain aspects, the powder is storage stable for at least or about 1, 2, 3, 4, 5, 6, 7, 8, 9, 10, 11, 12, 13, 14, 15, 16, 17, 18, 19, 20, 21, 22, 23, or 24 months at a temperature less than or about 8° C.

A liquid composition comprising water and the presently disclosed product or the presently disclosed dried powder is provided herein. In some aspects, the liquid composition comprises about 0.95 mL to about 1.5 mL water, optionally, about 1.0 mL water. In certain aspects, the liquid composition comprises at least or about $1 \times 10^6$ PFU live, attenuated virus (e.g., talimogene laherparepvec) per mL liquid composition and/or has a pH of about 7.4. In other aspects, the liquid composition comprises at least or about $1 \times 10^8$ PFU live, attenuated virus (e.g., talimogene laherparepvec) per mL liquid composition and/or has a pH of about 7.4.

A powder comprising a live, attenuated virus is furthermore provided by the present disclosure. In exemplary embodiments, the powder additionally comprises a human serum albumin (e.g., rHSA), a sugar other than lactose, a sugar alcohol, a source of phosphate, a source of chloride, wherein the composition is substantially free of lactose, gelatin, antibiotic, and free amino acids. Optionally, the powder comprises about 24.66 wt % to about 30.14 wt % rHSA. In exemplary instances, the sugar is sucrose and optionally is present in an amount of about 2.5 wt % to about 7.5 wt %, optionally, about 4.68 wt % to about 5.72 wt %. In certain instances, the sugar alcohol present in the powder is sorbitol and optionally is present in an amount of about 25 wt % to about 33 wt %, or about 35.76 wt % to about 43.7 wt %. In certain aspects, the source of phosphate is potassium phosphate and the powder comprises about 15 wt % to about 25 wt % potassium phosphate, optionally, about 17.87 wt % to about 21.85 wt %. In various aspects, the source of chloride is sodium chloride and the powder comprises about 5 wt % to about 10 wt % sodium chloride, optionally, about 7.0 wt % to about 8.6 wt % sodium chloride. In exemplary instances, the powder, upon the addition of about 1 mL water, makes a liquid composition comprising about 80 mM to about 85 mM potassium phosphate, about 95 mM to about 100 mM sodium chloride, about 2.8% (w/v) to about 3.0% (w/v) sorbitol, about 0.36% (w/v) to about 0.40% (w/v) sucrose, and about 1.98% (w/v) to about 2.02% (w/v) recombinant HSA.

The present disclosure also provides methods of preparing an oncolytic virus for administration to a human subject, comprising adding water to any one of the presently disclosed powders, optionally, wherein about 1.0 mL to about 1.2 mL water is added to the powder.

Further provided is a method of treating melanoma in a human subject, comprising adding water to any one of the presently disclosed powders, optionally, wherein about 1.0 mL to about 1.2 mL water is added to the powder, to obtain a liquid composition and injecting the liquid composition into the human subject.

DETAILED DESCRIPTION

Figure 1:
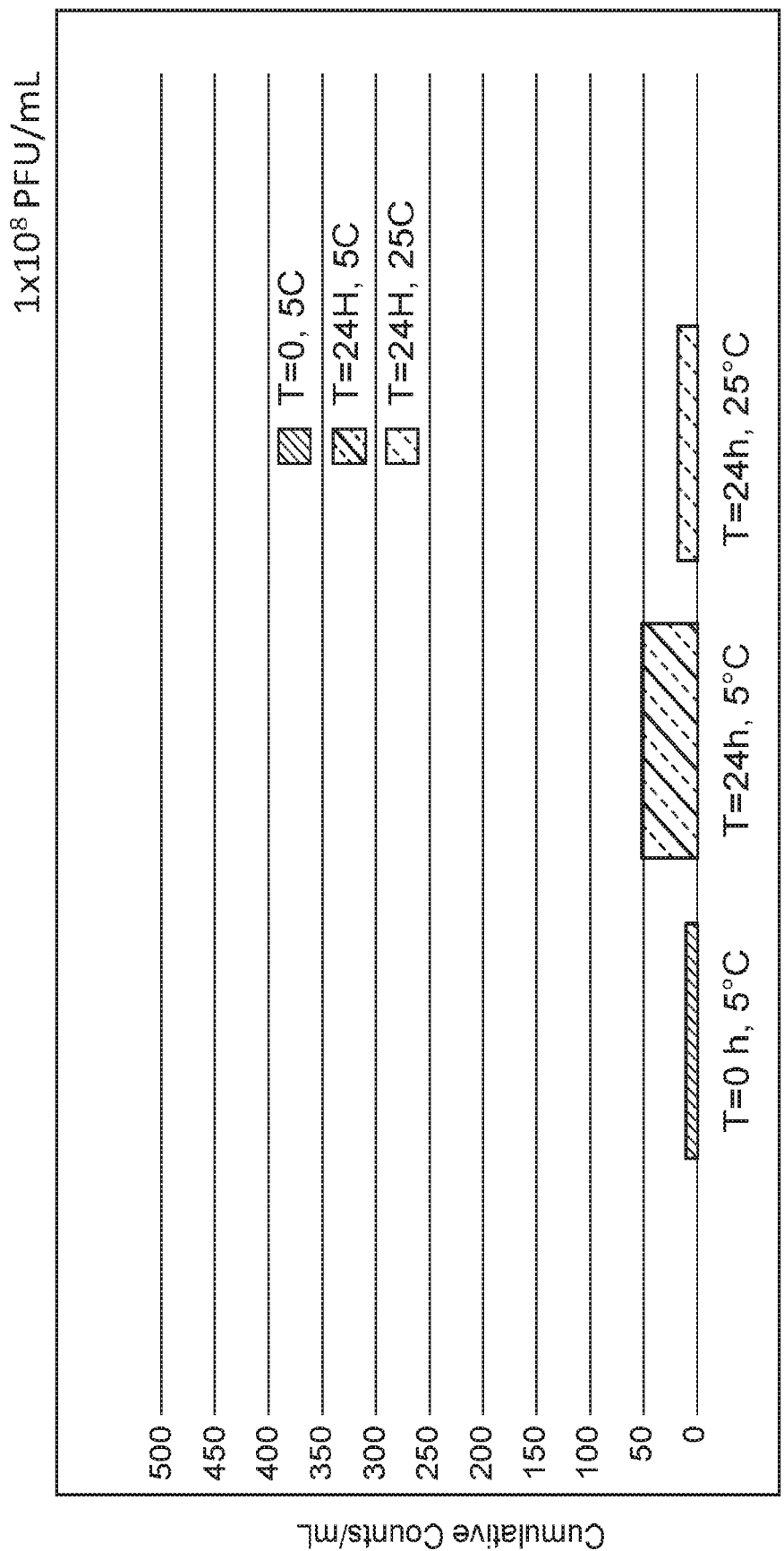
FIG. 1 is a graph of cumulative counts/mL depicting the quantity of subvisible particles >10 μm in reconstituted material formulated to contain 1×10$^8$ PFU/mL.

Provided herein are live virus compositions which are amenable to lyophilization or freeze-drying. Related powders and freeze-dried or lyophilized products are additionally provided. Such powders and products are advantageously storage-stable marked by an enhanced shelf-life, and characterized by a minimal or reduced loss of potency of the live virus upon lyophilization or freeze-drying. Also, the presently disclosed liquid compositions in various aspects adequately stabilize a live, attenuated virus in both the lyophilized and liquid states.

The present disclosure provides a liquid composition comprising a live, attenuated virus, human serum albumin (e.g., rHSA), a sugar other than lactose, a sugar alcohol, a source of phosphate, and a source of chloride. In various aspects, the liquid composition comprises the live, attenuated virus, HSA (e.g., rHSA), sucrose, sorbitol, potassium phosphate, and sodium chloride. In exemplary aspects, the liquid composition comprises about 18 mg/mL to about 22 mg/mL HSA (e.g., rHSA) or about 1.0% to about 3.0% (w/v) HSA (e.g., rHSA). In various instances, the liquid composition comprises about 3.4 mg/mL to about 4.2 mg/mL sucrose or about 0.25% to about 0.45% (w/v) sucrose. In some aspects, the liquid composition comprises about 26 mg/mL to about 31.9 mg/mL sorbitol or about 2.0% to about 4.0% (w/v) sorbitol. In various aspects, the liquid composition comprises about 13 mg/mL to about 16 mg/mL potassium phosphate or about 60 mM to about 100 mM potassium phosphate. In certain aspects, the liquid composition comprises about 5.1 mg/mL to about 6.3 mg/mL sodium chloride or about 80 to about 110 mM sodium chloride. Accordingly, provided herein is a liquid composition comprising a live, attenuated HSV-1 (e.g., talimogene laherparepvec), about 18 mg/mL to about 22 mg/mL HSA (e.g., rHSA), about 3.4 mg/mL to about 4.2 mg/mL sucrose, about 26 mg/mL to about 31.9 mg/mL sorbitol, about 13 mg/mL to about 16 mg/mL potassium phosphate, and about 5.1 mg/mL to about 6.3 mg/mL sodium chloride. Further provided is a liquid composition comprising a live, attenuated HSV-1 (e.g., talimogene laherparepvec), about 1.0% to about 3.0% (w/v) HSA (e.g., rHSA), about 0.25% to about 0.45% (w/v) sucrose, about 2.0% to about 4.0% (w/v) sorbitol, about 60 mM to about 100 mM potassium phosphate, and about 80 to about 110 mM sodium chloride. As used herein, the term "about" refers to a variation of 5% from the indicated values, or in case of a range of values, means a 5% variation from both the lower and upper limits of such ranges.

The liquid compositions of the present disclosure are, in exemplary embodiments, aqueous solutions, sterilized, e.g., filter sterilized, and/or substantially free of bacteria and endotoxins.

Human Serum Albumin (HSA)

In various aspects, the liquid composition comprises an albumin, optionally, human serum albumin (HSA). HSA is the most abundant protein found in human blood plasma. In various aspects, the liquid composition comprises recombinant HSA. As used herein, the term "recombinant" in the context of "HSA" means that the HSA is a genetically engineered product or made by recombinant production methods. A recombinant HSA is not derived from (isolated or purified from) a natural product (e.g., human plasma). Rather, genetically engineered cells can be used to produce the HSA. In various instances, the liquid composition comprises rHSA and optionally, the rHSA is produced using a yeast-based expression. In various aspects, the presently disclosed liquid composition comprises less than about 50 mg/mL, less than about 45 mg/mL, less than about 40 mg/mL, less than about 35 mg/mL, or less than about 30 mg/mL HSA (e.g., rHSA). In various aspects, the presently disclosed liquid composition comprises greater than about 1 mg/mL, greater than about 2 mg/mL, greater than about 3 mg/mL, greater than about 4 mg/mL, greater than about 5 mg/mL, greater than about 10 mg/mL, greater than about 15 mg/mL, or greater than about 20 mg/mL HSA (e.g., rHSA). Optionally, the liquid composition comprises greater than about 5 mg/mL and less than about 25 mg/mL HSA (e.g., rHSA), optionally, greater than about 10 mg/mL and less than about 25 mg/mL HSA (e.g., rHSA) or greater than about 15 mg/mL and less than about 25 mg/mL HSA (e.g., rHSA). In various instances, the liquid composition comprises about 17.5 mg/mL to about 22.5 mg/mL HSA (e.g., rHSA), e.g., about 20 mg/mL±2 mg/mL HSA (e.g., rHSA), optionally, about 20 mg/mL±1 mg/mL HSA (e.g., rHSA). In one embodiment, the liquid composition comprises about 20 mg/mL HSA (e.g., rHSA). In various aspects, the presently disclosed liquid composition comprises less than about 20% (w/v) (e.g., less than about 15% (w/v), less than about 10%

(w/v), less than about 5% (w/v)) HSA (e.g., rHSA). In some aspects, the presently disclosed liquid composition comprises less than 3% (w/v) and more than 0.1% (w/v), optionally about 1.8% (w/v) to about 2.2% (w/v) HSA (e.g., rHSA). In some aspects, the presently disclosed liquid composition comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5% (w/v) HSA (e.g., rHSA). In some aspects, the presently disclosed liquid composition comprises about 2.0% (w/v) HSA (e.g., rHSA). In some aspects, the liquid composition comprises less than about 5 mM HSA (e.g., rHSA) and greater than about 0.001 mM HSA (e.g., rHSA), e.g., about 0.001 mM to about 4 mM, about 0.001 mM to about 3 mM, about 0.001 mM to about 2 mM, about 0.001 mM to about 1 mM, or about 0.001 to about 0.5 mM. In various aspects, the HSA (e.g., rHSA) is present in the liquid composition in an amount of about 0.01 mM to about 1 mM or about 0.05 mM to about 0.5 mM, optionally, about 0.3 mM HSA (e.g., rHSA).

Sugars

In various aspects, the liquid composition comprises a sugar and the sugar is other than lactose. Advantageously, the composition, and its related products, of the present disclosure are amenable to administration to those who have a lactose allergy or lactose intolerance. In some instances, the sugar is dextrose, fructose, galactose, glucose, raffinose, trehalose, or sucrose. In various aspects, the sugar of the liquid composition is sucrose. In various aspects, the sugar (e.g., sucrose) is present in the liquid composition at an amount less than about 50 mg/mL, less than about 45 mg/mL, less than about 40 mg/mL, less than about 35 mg/mL, less than about 30 mg/mL, less than about 25 mg/mL, or less than about 20 mg/mL. In some aspects, the liquid composition comprises less than about 15 mg/mL sugar (e.g., sucrose), less than about 10 mg/mL sugar (e.g., sucrose) or less than about 5 mg/mL sugar (e.g., sucrose). In various aspects, the presently disclosed liquid composition comprises greater than about 1 mg/mL, greater than about 2 mg/mL, greater than about 3 mg/mL sugar (e.g., sucrose), optionally, the liquid composition comprises about 2 mg/mL to about 5 mg/mL. In some aspects, the liquid composition comprises less than about 3.8 mg/mL±0.38 mg/mL sucrose. In other aspects, the liquid composition comprises about 3.8 mg/mL sucrose. In various aspects, the presently disclosed liquid composition comprises less than about 10% (w/v) (e.g., less than about 9% (w/v), less than about 8% (w/v), less than about 7% (w/v), less than about 6% (w/v), less than about 5% (w/v), less than about 4% (w/v), less than about 3% (w/v), less than about 2% (w/v), less than about 1% (w/v)) sugar (e.g., sucrose). In some aspects, the presently disclosed liquid composition comprises less than 0.5% (w/v) and more than 0.1% (w/v), optionally about 0.30% (w/v) to about 0.42% (w/v) sugar (e.g., sucrose). In some aspects, the presently disclosed liquid composition comprises about 0.38% (w/v) sugar (e.g., sucrose). In some aspects, the liquid composition comprises less than about 50 mM sugar (e.g., sucrose) and greater than about 1 mM sugar (e.g., sucrose), e.g., about 1 mM to about 40 mM, about 1 mM to about 30 mM, about 1 mM to about 20 mM, about 1 mM to about 15 mM, about 5 mM to about 40 mM, about 5 mM to about 30 mM, about 5 mM to about 20 mM, about 5 mM to about 15 mM. In various aspects, the sugar (e.g., sucrose) is present in the liquid composition in an amount of about 5 mM to about 15 mM or about 10 mM to about 15 mM, optionally, about 11 mM sugar (e.g., sucrose).

Sugar Alcohols

In various aspects, the liquid composition comprises a sugar alcohol, e.g., mannitol, sorbitol, xylitol, maltitol, maltitol syrup, lactitol, erythritol, isomalt, and hydrogenated starch hydrosylate. In various instances, the sugar alcohol of the liquid composition is sorbitol. In certain aspects, the liquid composition comprises greater than about 5 mg/mL mg sugar alcohol (e.g., sorbitol) and less than about 50 mg/mL sugar alcohol (e.g., sorbitol). In certain aspects, the liquid composition comprises greater than about 15 mg/mL, greater than about 20 mg/mL, or greater than about 25 mg/mL sugar alcohol (e.g., sorbitol). In some aspects, the liquid composition comprises less than about 45 mg/mL sugar alcohol (e.g., sorbitol), less than about 40 mg/mL sugar alcohol (e.g., sorbitol), or less than about 35 mg/mL sugar alcohol (e.g., sorbitol). In various instances, the liquid composition comprises about 26 mg/mL to about 32 mg/mL sugar alcohol (e.g., sorbitol). In certain instances, the liquid composition comprises about 29 mg/mL sugar alcohol (e.g., sorbitol). In various aspects, the presently disclosed liquid composition comprises less than about 10% (w/v) (e.g., less than about 9% (w/v), less than about 8% (w/v), less than about 7% (w/v), less than about 6% (w/v), less than about 5% (w/v), less than about 4% (w/v), or less than about 3% (w/v) sugar alcohol (e.g., sorbitol). In some aspects, the presently disclosed liquid composition comprises less than 3.5% (w/v) and more than 2.5% (w/v), optionally about 2.6% (w/v) to about 3.2% (w/v) sugar alcohol (e.g., sorbitol). In some aspects, the presently disclosed liquid composition comprises about 2.9% (w/v) sugar alcohol (e.g., sorbitol). In some aspects, the liquid composition comprises less than about 500 mM sugar alcohol (e.g., sorbitol) and greater than about 50 mM sugar alcohol (e.g., sorbitol), e.g., about 50 mM to about 400 mM, about 50 mM to about 300 mM, about 50 mM to about 200 mM, about 75 mM to about 200 mM, about 100 mM to about 200 mM, about 125 mM to about 175 mM, about 150 mM to about 170 mM. In various aspects, the sugar alcohol (e.g., sorbitol) is present in the liquid composition in an amount of about 140 mM to about 175 mM or about 150 mM to about 167 mM, optionally, about 159 mM sugar alcohol (e.g., sorbitol).

Phosphate Sources

In various aspects, the liquid composition of the present disclosure comprises a source of phosphate. The source may be one of the following: Aluminum phosphate, Bone Phosphate, Calcium phosphate, Calcium Orthophosphate, Calcium Phosphate Dibasic Anhydrous, Calcium Phosphate-Bone Ash, Calcium Phosphate Dibasic Dihydrate, Calcium Phosphate Dibasique Anhydre, Calcium Phosphate Dibasique Dihydrate, Calcium Phosphate Tribasic, Calcium Phosphate Tribasique, Dibasic Calcium Phosphate Dihydrate, Di-Calcium Phosphate, Dicalcium Phosphate, Dicalcium Phosphates, Neutral Calcium Phosphate, Orthophosphate de Calcium, Phosphate d'Aluminium, Phosphate de Calcium, Phosphate de Magnesium, Phosphate Neutre de Calcium, Phosphate d'Os, Phosphate Tricalcium, Precipitated Calcium Phosphate, Precipitation du Phosphate de Calcium, Précipité de Phosphate de Calcium, Tertiary Calcium Phosphate, Tricalcium Phosphate, Whitlockite, Magnesium Phosphate, Merisier, Potassium phosphate, Dibasic Potassium Phosphate, Dipotassium Hydrogen Orthophosphate, Dipotassium Monophosphate, Dipotassium Phosphate, Monobasic Potassium Phosphate, Potassium Acid Phosphate, Potassium Biphosphate, Potassium Dihydrogen Orthophosphate, Potassium Hydrogen Phosphate, Phosphate de Dipotassium, Phosphate d'Hydrogène de Potassium, Phosphate de Potassium, Phosphate de Potassium Dibasique, Phosphate de Potassium Monobasique, Sodium phosphate, Anhydrous Sodium Phosphate, Dibasic Sodium Phosphate, Disodium Hydrogen Orthophosphate, Disodium Hydrogen Orthophosphate Dodecahydrate, Disodium Hydrogen Phosphate, Disodium Phosphate, Phosphate of Soda, Sales de Fosfato, Sels de Phosphate, Sodium Orthophosphate, Orthophosphate Disodique d'Hydrogene, Phosphate Disodique d'Hydrogène, Orthophosphate de Sodium, Phosphate de Sodium Anhydre, Phosphate de Sodium Dibasique, and Phosphorus. In some aspects, the source of phosphate present in the liquid composition is sodium phosphate or potassium phosphate. In some a particular aspect, the source of phosphate present in the liquid composition is potassium phosphate. In various instances, the liquid composition comprises greater than about 5 mg/mL and less than about 45 mg/mL source of phosphate (e.g. potassium phosphate), optionally, less than about 40 mg/mL source of phosphate (e.g. potassium phosphate) (e.g., less than about 30 mg/mL source of phosphate (e.g. potassium phosphate), less than about 20 mg/mL source of phosphate (e.g. potassium phosphate), or about 13.5 mg to about 16 mg/mL source of phosphate (e.g. potassium phosphate). In a particular embodiment, the liquid composition comprises about 14.5 mg/mL of phosphate (e.g., potassium phosphate). In various instances, the liquid composition comprises greater than about 25 mM and less than about 500 mM source of phosphate (e.g. potassium phosphate), e.g., about 25 mM to about 400 mM, about 25 mM to about 300 mM, about 25 mM to about 200 mM, about 25 mM to about 100 mM, about 50 mM to about 150 mM, about 50 mM to about 100 mM. Optionally, less than about 100 mM source of phosphate (e.g. potassium phosphate), (e.g., less than about 90 mM source of phosphate (e.g. potassium phosphate), greater than about 50 mM and less than about 90 mM, about 60 mM to about 90 mM, about 70 mM to about 90 mM, about 80 mM to about 85 mM source of phosphate (e.g. potassium phosphate), or about 75 mM to about 92 mM source of phosphate (e.g. potassium phosphate). In a particular embodiment, the liquid composition comprises about 83 mM source of phosphate (e.g. potassium phosphate).

Chloride Sources

In various aspects, the liquid composition of the present disclosure comprises a source of chloride (e.g., sodium or potassium chloride). In some instances, the source of chloride is sodium chloride. In exemplary aspects, the source of chloride (e.g., NaCl) is present in an amount greater than about 1 mg/mL and less than about 20 mg/mL source of chloride (e.g., NaCl) (e.g., about 1 mg/mL to about 15 mg/mL, about 1 mg/mL to about 10 mg/mL, about 1 mg/mL to about 7.5 mg/mL, about 3 mg/mL to about 15 mg/mL, about 3 mg/mL to about 10 mg/mL, about 3 mg/mL to about 7.5 mg/mL. In some aspects, the liquid composition comprises less than about 15 mg/mL source of chloride (e.g., NaCl) or less than about 10 mg/mL source of chloride (e.g., NaCl), e.g., about 3 mg to about 7 mg/mL source of chloride (e.g., NaCl), optionally, about 5.7 mg/mL.

In various instances, the liquid composition comprises greater than about 25 mM and less than about 500 mM source of chloride (e.g., NaCl), e.g., about 25 mM to about 400 mM, about 25 mM to about 300 mM, about 25 mM to about 200 mM, about 25 mM to about 150 mM, about 50 mM to about 150 mM, about 75 mM to about 125 mM. Optionally, less than about 150 mM source of chloride (e.g., NaCl), (e.g., less than about 125 mM source of chloride (e.g., NaCl), greater than about 50 mM and less than about 125 mM, about 60 mM to about 120 mM, about 70 mM to about 110 mM, about 80 mM to about 110 mM source of chloride (e.g., NaCl), or about 88 mM to about 108 mM source of chloride (e.g., NaCl), optionally, about 98 mM.

Lactose-, Gelatin-, Antibiotic-, and Free Amino Acid-Free

In exemplary aspects, the liquid composition is substantially free of added lactose. In exemplary aspects, the liquid composition is substantially free of added gelatin. In exemplary aspects, the liquid composition is substantially free of added antibiotics (e.g., neomycin, kanamycin, gentamicin, ampicillin, carbenicillin, cefotaxime, fosmidomycin, actinomycin, polymyxin, penicillin, streptomycin). In exemplary aspects, the liquid composition is substantially free of added free amino acids. For instance, the liquid composition is not made with any lactose, any gelatin, any antibiotic, or any free amino acids. In certain aspects, none of these components (none of lactose, gelatin, antibiotics, and free amino acids) were added when making the presently disclosed liquid composition or powder or lyophilizate.

As used herein, the term "free amino acids" refers to added unbound or unlinked amino acids or amino acids that are not peptide bonded to another amino acid. In various instances, the liquid composition is substantially free of any "free amino acids" meaning that free amino acids were not added to the liquid composition as a component. The "free amino acids" do not refer to any unbound or unlinked amino acids present in the composition due to e.g., degradation of the HSA (e.g., rHSA). In exemplary aspects, the liquid composition is substantially free of Glu or His.

As used herein "substantially free" means less than 0.01 wt % or less than 0.01% (w/v) or less than 100 ppm. In certain aspects, the liquid composition comprises not more than about 0.01 mM of any of lactose, gelatin, antibiotic, and free amino acids, optionally, not more than about 0.001 mM any of lactose, gelatin, antibiotic, and free amino acids.

pH and Osmolality

In various aspects, the liquid composition (e.g., reconstituted lyophilized composition) has a pH of about 7.0 to about 7.8, optionally, about 7.2 to about 7.6 (e.g., 7.2, 7.3, 7.4, 7.5, 7.6). In various instances, the pH of the liquid composition is about 7.4±0.05.

In various aspects, the liquid composition has an osmolality less than about 700 mOsm/kg, optionally, less than bout 650 mOsm/kg (e.g., an osmolality less than about 600 mOsm/kg, optionally, about 525 mOsm/kg to about 575 mOsm/kg). In exemplary aspects, the osmolality of the liquid composition is about 540 mOsm/kg to about 560 mOsm/kg, or about 550 mOsm/kg.

Traditional frozen formulations may have osmolalities in the range of 700-900 mOsm/kg. The lyophilized formulations of the present invention, however, demonstrate the desired properties (e.g., improved potency after lyophilization and increased shelf life at temperatures suitable for a supply chain) with an osmolality (e.g., upon reconstitution) below that of such traditional frozen formulations. The lower osmolality of the reconstituted lyophilized formulations is not expected to alter the local tolerability of the lyophilized drug product after administration or the local biological effect, and may improve local tolerability with respect to, e.g., discomfort, irritation, sensation of heat or pain after injection.

Live Viruses

The herpes virus particle is a complex structure consisting of a double-stranded DNA genome packaged within an icosahedral protein capsid that is enveloped in a cell-derived membrane bilayer. Sandwiched between the capsid and the lipid envelope is a layer of viral proteins known as the tegument [Roizman B (1982) The Family Herpesviridae: General Description, taxonomy and classification. The Viruses, Vol A, Herpesviruses. New York: Plenum Press, Mettenleiter T C (2002) Herpesvirus assembly and egress. Journal of virology 76: 1537-1547.]. The presence of a membrane envelope is a distinguishing feature of many different types of animal viruses. In formulating compositions to stabilize live viruses, the lipid envelope appears to confer significant physical instability to the viral particle, making it difficult to stabilize this class of viruses, especially when compared to non-enveloped mammalian viruses such as adenovirus, reovirus, and poliovirus. For example, at 2-8° C. storage, Adenovirus Type 5 has been shown to be stable for 2 years, and polioviruses and reoviruses for at least 1 year [Sokhey et al., (1988). Vaccine 6: 12-13; Berard and Coombs (2009). Current protocols in microbiology: 15C-1; and Evans R K, et al. (2004) J Pharm Sci 93: 2458-2475]. Poxvirus appears to be the only enveloped animal virus exhibiting similar extents of storage stability at similar temperatures. However, poxvirus is structurally distinct from other enveloped animal viruses as it contains a double envelope and other structural differences [Condit et al., (2006). Advances in virus research 66: 31-124, Moss B (1987) The molecular biology of poxviruses. The Molecular Basis of Viral Replication. Springer. pp. 499-516]. Indeed, poxviruses are remarkably stable as demonstrated by the long term storage observed in archived tissues, environmental samples, and lab storage of dried samples at 2-8° C. for over 60 years [McCollum et al., (2014) Poxvirus viability and signatures in historical relics. Emerging infectious diseases 20: 177; FDA found more than smallpox vials in storage room (n.d.). Available: https://www.washingtonpost.com/national/health-science/fda-found-more-than-smallpox-vials-in-storage-room/2014/07/16/850d4b12-0d22-11e4-8341-b8072b1e7348_story.html. Accessed 7 Nov. 2015; CDC Media Statement on Newly Discovered Smallpox Specimens (n.d.). Available: http://www.cdc.gov/media/releases/2014/s0708-NIH.html. Accessed 7 Nov. 2015; Rheinbaben et al., (2007) Environmental resistance, disinfection, and sterilization of poxviruses. Poxviruses. Springer. pp. 397-405; and Essbauer et al., (2007) Long-Lasting Stability of Vaccinia Virus (Orthopoxvirus) in Food and Environmental Samples. Zoonoses and public health 54: 118-124].

Oncolytic viruses have demonstrated anti-cancer activity in a variety of tumor types. Oncolytic immunotherapy is a treatment modality which uses replication competent oncolytic viruses that selectively infect and damage cancerous tissues without causing harm to normal tissues. Ongoing studies are using a variety of engineered viruses not limited to herpes simplex virus (HSV), vaccinia, and reovirus.

In exemplary aspects, the oncolytic virus is derived from a herpes simplex virus 1 (HSV-1) or herpes simplex 2 (HSV-2) strain, or from a derivative thereof, preferably HSV-1. Derivatives include inter-type recombinants containing DNA from HSV-1 and HSV-2 strains. Such inter-type recombinants are described in the art, for example in Thompson et al., (1998) Virus Genes 1(3); 275286, and Meignier et al., (1998) J. Infect. Dis.159; 602614.

Herpes simplex virus strains may be derived from clinical isolates. Such strains are isolated from infected individuals, such as those with recurrent cold sores. Clinical isolates may be screened for a desired ability or characteristic such as enhanced replication in tumor and/or other cells in vitro and/or in vivo in comparison to standard laboratory strains, as described in U.S. Pat. No. 7,063,835 and U.S. Pat. No. 7,223,593, each of which are incorporated by reference in their entirety. In one embodiment the herpes simplex virus is a clinical isolate from a recurrent cold sore. Additional herpes simplex virus 1 virus strains include, but are not limited to, strain JS1, strain 17+, strain F, strain KOS, and strain Patton.

Examples of HSV genes that can be modified include virulence genes encoding proteins such as ICP34.5 (γ34.5). ICP34.5 acts as a virulence factor during HSV infection, limits replication in non-dividing cells and renders the virus non-pathogenic. Another HSV gene that can be modified is the gene encoding ICP47. ICP47 down-regulates major histocompatibility complex (MHC) class I expression on the surface of infected host cells and MHC Class I binding to transporter associated with antigen presentation (TAP). Such actions block antigenic peptide transport in the endoplasmic reticulum and loading of MHC class I molecules. Another HSV gene that can be modified is ICP6, the large subunit of ribonucleotide reductase, involved in nucleotide metabolism and viral DNA synthesis in non-dividing cells but not in dividing cells. Thymidine kinase, responsible for phosphorylating acyclovir to acyclovir-monophosphate, virion trans-activator protein vmw65, glycoprotein H, vhs, ICP43, and immediate early genes encoding ICP4, ICP27, ICP22 and/or ICP0, may be modified as well (in addition or alternative to the genes referenced above).

Herpes virus strains and how to make such strains are also described in U.S. Pat. Nos. 5,824,318; 6,764,675; 6,770,274; 7,063,835; 7,223,593; 7,749,745; 7,744,899; 8,273,568; 8,420,071; and 8,470,577; WIPO Publication Numbers WO199600007; WO199639841; WO199907394; WO200054795; WO2006002394; and WO2013067950; Chinese Patent Numbers CN128303, CN10230334 and CN 10230335; Varghese and Rabkin, (2002) Cancer Gene Therapy 9:967-97, and Cassady and Ness Parker, (2010) The Open Virology Journal 4:103-108, which are incorporated by reference in their entirety.

In one embodiment, the oncolytic virus is talimogene laherparepvec (IMLYGIC®), derived from a clinical strain (HSV-1 strain JS1) deposited at the European collection of cell cultures (ECAAC) under accession number 01010209. In talimogene laherparepvec, the HSV-1 viral genes encoding ICP34.5 and ICP47 have been functionally deleted. Functional deletion of ICP47 leads to earlier expression of US11, a gene that promotes virus growth in tumor cells without decreasing tumor selectivity. The coding sequence for human GM-CSF, has been inserted into the viral genome at the former ICP34.5 sites (see Liu et al., Gene Ther 10: 292-303, 2003).

Other examples of oncolytic viruses include RP1 (HSV-1/ICP34.5⁻/ICP47⁻/GM-CSF/GALV-GP R(−); RP-2 (HSV-1/ICP34.5⁻/ICP47⁻/GM-CSF/GALV-GP R(−)/anti-CTLA-4 binder; and RP3 (HSV-1/ICP34.5⁻/ICP47⁻/GM-CSF/GALV-GP R(−)/anti-CTLA-4 binder/co-stimulatory ligands (e.g., CD40L, 4-1BBL, GITRL, OX40L, ICOSL)). In such oncolytic viruses, GALV (gibbon ape leukemia virus) has been modified with a specific deletion of the R-peptide, resulting in GALV-GP R(−). Such oncolytic virsues are discussed in WO2017118864, WO2017118865, WO2017118866, WO2017118867, and WO2018127713A1, each of which is incorporated by reference in its entirety.

Additional examples of oncolytic viruses include NSC-733972, HF-10, BV-2711, JX-594, Myb34.5, AE-618, Brainwel™, and Heapwel™, Cavatak® (coxsackievirus, CVA21), HF-10, Seprehvir®, Reolysin®, enadenotucirev, ONCR-177, and those described in U.S. patent application Ser. No. 10,105,404, WO2018006005, WO2018026872A1, and WO2017181420, each of which is incorporated by reference in its entirety.

Further examples of oncolytic viruses include:

[A] G207, an oncolytic HSV-1 derived from wild-type HSV-1 strain F having deletions in both copies of the major determinant of HSV neurovirulence, the ICP 34.5 gene, and an inactivating insertion of the *E. coli* lacZ gene in UL39, which encodes the infected-cell protein 6 (ICP6), see Mineta et al. (1995) Nat Med. 1:938-943.

[B] OrienX010, a herpes simplex virus with deletion of both copies of γ34.5 and the ICP47 genes as well as an interruption of the ICP6 gene and insertion of the human GM-CSF gene, see Liu et al., (2013) World Journal of Gastroenterology 19(31): 5138-5143.

[C] NV1020, a herpes simples virus with the joint region of the long (L) and short (S) regions is deleted, including one copy of ICP34.5, UL24, and UL56.34,35. The deleted region was replaced with a fragment of HSV-2 US DNA (US2, US3 (PK), gJ, and gG), see Todo, et al. (2001) Proc Natl Acad Sci USA. 98:6396-6401.

[D] M032, a herpes simplex virus with deletion of both copies of the ICP34.5 genes and insertion of interleukin 12, see Cassady and Ness Parker, (2010) The Open Virology Journal 4:103-108.

[E] ImmunoVEX HSV2, is a herpes simplex virus (HSV-2) having functional deletions of the genes encoding vhs, ICP47, ICP34.5, UL43 and US5.

[F] OncoVEX$^{GALV/CD}$, is also derived from HSV-1 strain JS1 with the genes encoding ICP34.5 and ICP47 having been functionally deleted and the gene encoding cytosine deaminase and gibbon ape leukaemia fusogenic glycoprotein inserted into the viral genome in place of the ICP34.5 genes.

The herpes simplex viruses of the invention may also comprise one or more heterologous genes. Heterologous gene refers to a gene to be introduced to the genome of a virus, wherein that gene is not normally found in the virus' genome or is a homolog of a gene expressed in the virus from a different species which has a different nucleic acid sequence and acts via a different biochemical mechanism. The heterologous genes may encode one or more proteins, for example, a cytotoxin, an immunomodulatory protein (i.e., a protein that either enhances or suppresses a host immune response to an antigen), a tumor antigen, prodrug activator, a tumor suppressor, a prodrug converting enzyme, proteins capable of causing cell to cell fusion, a TAP inhibitor antisense RNA molecule, or a ribozyme. Examples of immunomodulatory proteins include, for example, cytokines. Cytokines include an interleukins, such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-20; α, β or γ-interferons, tumor necrosis factor alpha (TNFα), CD40L, granulocyte macrophage colony stimulating factor (GM-CSF), macrophage colony stimulating factor (M-CSF), and granulocyte colony stimulating factor (G-CSF), chemokines (such as neutrophil activating protein (NAP), macrophage chemoattractant and activating factor (MCAF), RANTES, and macrophage inflammatory peptides MIP-1a and MIP-1b), complement components and their receptors, immune system accessory molecules (e.g., B7.1 and B7.2), adhesion molecules (e.g., ICAM-1, 2, and 3), and adhesion receptor molecules. Tumor antigens include the E6 and E7 antigens of human papillomavirus, EBV-derived proteins, mucins, such as MUC1, melanoma tyrosinase, and MZ2-E. Pro-drug activators include nitroeductase and cytochrome p450, tumour suppressors include p53. a prodrug converting enzymes include cytosine deaminase. Proteins capable of causing cell to cell fusion include gibbon ape leukaemia fusogenic glycoprotein. TAP inhibitors include the bovine herpesvirus (BHV) UL49.5 polypeptide. Antisense RNA molecules that can be used to block expression of a cellular or pathogen mRNA. RNA molecules that can be a ribozyme (e.g., a hammerhead or a hairpin-based ribozyme) designed either to repair a defective cellular RNA, or to destroy an undesired cellular or pathogen-encoded RNA.

Also included is insertion of multiple viral genes into the herpes simplex genome, such as insertion of one or more copies of the gene encoding viral protein Us 11.

The oncolytic viruses described herein (e.g., talimogene laherparepvec) can be used to treat a variety of tumor types including, but not limited to, melanoma, head and neck cancer, breast cancer (e.g., triple negative breast cancer), colorectal cancer, hepatocellular carcinoma, gastroesophageal cancer (e.g., adenocarcinoma or squamous cell carcinoma), non-small cell lung cancer, and clear cell renal cell carcinoma. In a particular embodiment, the tumor type is melanoma.

In various aspects, the liquid (e.g., reconstituted) composition comprises at least about $1 \times 10^5$ plaque forming unit/mL (PFU/mL). In exemplary aspects, the liquid (e.g., reconstituted) composition comprises at least at least about $2.0 \times 10^5$ PFU/mL, at least about $3.0 \times 10^5$ PFU/mL, at least about $4.0 \times 10^5$ PFU/mL, at least about $5.0 \times 10^5$ PFU/mL, at least about $6.0 \times 10^5$ PFU/mL, at least about $7.0 \times 10^5$ PFU/mL, at least about $8.0 \times 10^5$ PFU/mL, or at least about $9.0 \times 10^5$ PFU/mL. In certain aspects, the liquid composition (e.g., reconstituted) comprises at least about $1.0 \times 10^6$ PFU/mL to about $1.0 \times 10^8$ PFU/mL or $1.0 \times 10^6$ plaque forming unit/mL (PFU/mL) to about $1.0 \times 10^8$ PFU/mL, optionally, about $1.1 \times 10^6$ PFU/mL, at least about $1.2 \times 10^6$ PFU/mL, at least about $1.3 \times 10^6$ PFU/mL, at least about $1.4 \times 10^6$ PFU/mL, at least about $1.5 \times 10^6$ PFU/mL, at least about $1.6 \times 10^6$ PFU/mL, at least about $1.7 \times 10^6$ PFU/mL, at least about $1.8 \times 10^6$ PFU/mL, at least about $1.9 \times 10^6$ PFU/mL. In particular embodiments, the liquid (e.g., reconstituted) composition comprises about $1 \times 10^6$ PFU/mL or $1 \times 10^8$ PFU/mL.

Potency and Stability

Lyophilization is a process that removes water from samples. Lyophilization typically results in improved storage stability compared to storage in the liquid state. However, because lyophilization involves freezing and dehydration (by sublimation), it is also stressful process, particularly to biological agents such as enveloped viruses. While lyophilization can improve long-term stability, the process stress can also inactivate a significant portion of the agent of interest causing significant loss of potency. A satisfactory formulation will not only provide adequate liquid stability, and stability in the dried state, but will also minimize losses due to the lyophilization process.

It is a known challenge to develop formulations that stabilize labile agents (such enveloped viruses) simultaneously in both liquid and lyophilized states, as the optimal compositions for each state are mutually exclusive and thus, typically not ideal for the other. Nevertheless, for a lyophilized product it is important that a formulation adequately supports the stability of the active agent in both the liquid and lyophilized states. This is because nearly all stages of a manufacturing process preceding lyophilization occur in the liquid state and, thus, activity of the active ingredient must be preserved up to the point of lyophilization. Similarly, after lyophilization, if the product is to be reconstituted (e.g., for use as a liquid product), liquid stability is important in order to ensure potency is maintained for an appropriate duration to support subsequent handling and storage. In addition, the lyophilization process itself can be destructive to biological agents, particularly enveloped viruses, which are sensitive to osmotic stress and cryo-concentration effects that can occur during the freezing stage of lyophilization, as well as the dehydration effects that occur during the drying stages of lyophilization. Prior to the present disclosure, developing formulations that adequately stabilize a labile agent, such as an enveloped virus, in both the liquid and lyophilized states, remains a significant challenge. Without being bound to any particular theory, the presently disclosed liquid compositions overcome these challenges. The liquid compositions in various aspects, adequately stabilize a live, attenuated virus in both the liquid and lyophilized states.

In various instances, when the liquid composition is lyophilized or freeze-dried and later reconstituted with water to produce a reconstituted product, the potency of the live, attenuated virus in the reconstituted product is at least or about 20%, 25%, 30%, 35%, 40%, 45%, 50%, 55%, 60%, 65%, 70%, 75%, 80%, 85%, 90%, or 90% of the potency of the live, attenuated virus before the liquid composition is lyophilized. In some embodiments, the potency of the live, attenuated virus in the reconstituted product is at least or about 30%, 31%, 32%, 33%, 34%, 35%, 36%, 37%, 38%, 39%, 40%, 41%, 42%, 43%, 44%, 45%, 46%, 47%, 48%, 49%, or 50% of the potency of the live, attenuated virus before the liquid composition is lyophilized. In other embodiments, the potency of the live, attenuated virus in the reconstituted product is at least or about 30%, 31%, 32%, 33%, 34%, 35%, 36%, 37%, 38%, 39%, or 40%. In yet other embodiments, the potency of the live, attenuated virus in the reconstituted product is at least or about 35% of the potency of the live, attenuated virus before the liquid composition is lyophilized. In various instances, when the liquid composition is lyophilized or freeze-dried and later reconstituted with water to produce a reconstituted product, the potency of the live, attenuated virus in the reconstituted product exhibits less than 1-log loss in potency of the live, attenuated virus in the reconstituted product. In some embodiments, the reconstituted product exhibits less than about a 1-log, 0.9-log, 0.8-log, 0.7-log, 0.6-log, 0.5-log, 0.4-log, 0.3-log, 0.2-log or 0.1-log loss in potency of the live, attenuated virus in the reconstituted product. In specific embodiments, the reconstituted product exhibits less than about a 0.6-log, 0.5-log, or 0.4-log loss in potency of the live, attenuated virus in the reconstituted product. In specific embodiments, the reconstituted product exhibits less than about a 0.6-log, 0.5-log, or 0.4-log loss in potency of the live, attenuated virus in the reconstituted product. In another embodiment, the reconstituted product exhibits less than about a 0.5-log loss in potency of the live, attenuated virus in the reconstituted product.

In some aspects, the liquid composition is lyophilized or freeze-dried and later reconstituted with water to produce a reconstituted product, the potency of the live, attenuated virus in the reconstituted product is at least or about 20%, 25%, 30%, 35%, 40%, 45%, 50%, 55%, 60%, 65%, 70%, 75%, 80%, 85%, 90%, or 90% of the potency of the live, attenuated virus before the liquid composition is lyophilized. In some embodiments, the liquid composition is lyophilized or freeze-dried and later reconstituted with water to produce a reconstituted product, the potency of the live, attenuated virus in the reconstituted product is at least or about 30%, 31%, 32%, 33%, 34%, 35%, 36%, 37%, 38%, 39%, 40%, 41%, 42%, 43%, 44%, 45%, 46%, 47%, 48%, 49%, or 50% of the potency of the live, attenuated virus before the liquid composition is lyophilized. In other embodiments, the liquid composition is lyophilized or freeze-dried and later reconstituted with water to produce a reconstituted product, the potency of the live, attenuated virus in the reconstituted product is at least or about 30%, 31%, 32%, 33%, 34%, 35%, 36%, 37%, 38%, 39%, or 40%. In yet other embodiments, the liquid composition is lyophilized or freeze-dried and later reconstituted with water to produce a reconstituted product, the potency of the live, attenuated virus in the reconstituted product is at least or about 35% of the potency of the live, attenuated virus before the liquid composition is lyophilized. In various instances, when the liquid composition is lyophilized or freeze-dried and later reconstituted with water to produce a reconstituted product, the potency of the live, attenuated virus in the reconstituted product exhibits less than 1-log loss in potency of the live, attenuated virus in the reconstituted product. In some embodiments, the reconstituted product exhibits less than about a 1-log, 0.9-log, 0.8-log, 0.7-log, 0.6-log, 0.5-log, 0.4-log, 0.3-log, 0.2-log or 0.1-log loss in potency of the live, attenuated virus in the reconstituted product. In specific embodiments, the reconstituted product exhibits less than about a 0.6-log, 0.5-log, or 0.4-log loss in potency of the live, attenuated virus in the reconstituted product. In specific embodiments, the reconstituted product exhibits less than about a 0.6-log, 0.5-log, or 0.4-log loss in potency of the live, attenuated virus in the reconstituted product. In another embodiment, the reconstituted product exhibits less than about a 0.5-log loss in potency of the live, attenuated virus in the reconstituted product.

In various instances, when the liquid composition is lyophilized or freeze-dried the resulting lyophilized or freeze-dried product is shelf-stable or storage-stable. In exemplary aspects, the lyophilized or freeze-dried product may be stored long term at a temperature of about −25° C. to about 10° C., about −20° C. to about 8° C., about −15° C. to about 8° C., about −10° C. to about 8° C., about −10° C. to about 5° C., or about 2° C. to about 8° C. In other embodiments, the lyophilized or freeze-dried product may be stored long term at a temperature of about −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., or 10° C. The lyophilized or freeze-dried product may be stored at such temperatures for at least or about 1, 2, 3, 4, 5, 6, 7, 8, 9, 10, 11, 12, 13, 14, 15, 16, 17, 18, 19, 20, 21, 22, 23, or 24 months. In other embodiments, the lyophilized or freeze-dried product may be stored at such temperatures for at least or about 9-24 months, about 12-24 months, about 12-18 months, about 12-15 months, or about 10-15 months. Optionally, the lyophilized or freeze-dried product may be stored long term at a temperature of about 2° C. to about 8° C. for at least 12, 15, 18, 21, or 24 months.

Lyophilized and Freeze-Dried Products and Powders

The presently disclosed liquid compositions are amenable to dehydration, lyophilization or freeze-drying. When the liquid compositions are dehydrated, freeze-dried, or lyophilized, the resulting dehydrated, freeze-dried, or lyophilized product exhibits remarkable storage stability and an enhanced shelf-life. Once reconstituted, the product is characterized by a minimal or reduced loss of potency of the live virus. The present disclosure accordingly provides a product produced by dehydrating, freeze-drying or lyophilizing any one of the presently disclosed liquid compositions. The product in some aspects is a powder. In alternative aspects, the solid product may be described as a cake.

Also, relatedly, the present disclosure provides a powder or cake produced by a method comprising removing water (dehydrating, e.g., via lyophilization) from a composition comprising a live, attenuated virus, HSA (e.g., rHSA), a sugar other than lactose, a sugar alcohol, a source of phosphate, a source of chloride. Optionally, the composition is substantially free of lactose, gelatin, antibiotic, and free amino acids. In some aspects, the composition is frozen and the removal of water from the frozen composition occurs under a vacuum. Accordingly, in exemplary aspects, the method comprises freezing a liquid composition of the present disclosures, removing water from the frozen composition under a vacuum to effect sublimation of ice of the frozen composition to change into vapor without passing through the liquid phase. The method may comprise additional steps including, e.g., sterilizing the liquid composition by passing it through a 0.22 micron bacteria-retentive filter and/or filling the sterilized liquid composition into vials. In various aspects, the powder or cake is a lyophilizate or a lyophilized powder or lyophilized cake. In some aspects, the liquid composition comprises a live, attenuated HSV-1 (e.g., talimogene laherparepvec), about 18 mg/mL to about 22 mg/mL HSA (e.g., rHSA), about 3.4 mg/mL to about 4.2 mg/mL sucrose, about 26 mg/mL to about 31.9 mg/mL sorbitol, about 13 mg/mL to about 16 mg/mL potassium phosphate, and about 5.1 mg/mL to about 6.3 mg/mL sodium chloride. Accordingly, additionally provided herein is a powder or cake (e.g., a lyophilized powder or lyophilized cake) produced by a method comprising removing water (e.g., dehydrating, e.g., via lyophilization) from a composition comprising a live, attenuated HSV-1 (e.g., talimogene laherparepvec), about 18 mg/mL to about 22 mg/mL HSA (e.g., rHSA), about 3.4 mg/mL to about 4.2 mg/mL sucrose, about 26 mg/mL to about 31.9 mg/mL sorbitol, about 13 mg/mL to about 16 mg/mL potassium phosphate, and about 5.1 mg/mL to about 6.3 mg/mL sodium chloride. Optionally, the composition is substantially free of lactose, gelatin, antibiotic, and free amino acids. In some aspects, the composition is frozen to obtain a composition comprising ice prior to removing water, and, optionally, the method further comprises placing the composition under a vacuum after removing the water. In certain aspects, the powder is storage stable for at least or about 1, 2, 3, 4, 5, 6, 7, 8, 9, 10, 11, 12, 13, 14, 15, 16, 17, 18, 19, 20, 21, 22, 23, or 24 months at a temperature less than or about 8° C. In certain aspects, the powder is storage stable for at least or about 12, 15, 18, 21, or 24 months at a temperature less than or about 8° C.

A dehydrated product (e.g., a lyophilized product, a freeze-dried product), which may be in the form of a powder or a cake, comprising a live, attenuated virus is furthermore provided by the present disclosure. In exemplary embodiments, the product additionally comprises a HSA (e.g., rHSA), a sugar other than lactose, a sugar alcohol, a source of phosphate, a source of chloride, optionally, wherein the composition is substantially free of lactose, gelatin, antibiotic, and free amino acids. In various aspects, the product (e.g., powder or cake) comprises about 10 wt % to about 50 wt % HSA (e.g., rHSA), e.g., about 15 wt % to about 45 wt %, 20 wt % to about 40 wt %, 25 wt % to about 35 wt %, 25 wt % to about 30 wt %. In various aspects, the product comprises about 24.66 wt % to about 30.14 wt % HSA (e.g., rHSA) or less than 30 wt % HSA (e.g., rHSA), e.g., about 25%, about 26%, about 27%, about 28%, about 29% HSA (e.g., rHSA). In exemplary instances, the product (e.g., powder or cake) comprises less than about 10% sugar, optionally, about 2.5 wt % to about 7.5 wt % sugar (e.g. sucrose), optionally, about 4.68 wt % to about 5.72 wt %. In exemplary instances, the sugar is sucrose and optionally is present in an amount of about 2.5 wt % to about 7.5 wt %, optionally, about 4.68 wt % to about 5.72 wt % (e.g., about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %). In exemplary instances, the product (e.g., powder or cake) comprises less than about 50 wt % sugar alcohol (e.g., sorbitol). In some aspects, the product comprises less than about 45 wt % and optionally more than about 5 wt %, more than about 10 wt %, more than about 15 wt %, more than about 20 wt %, more than about 25 wt %, or more than about 30 wt %. In certain instances, the sugar alcohol (e.g., sorbitol) is present in the product at an amount of about 35 wt % to about 45 wt %, e.g., about 36 wt %, about 37 wt %, about 38 wt %, about 39 wt %, about 40 wt %, about 41 wt %, about 42 wt %, about 43 wt %, about 44 wt %, about 45 wt %. In exemplary instances, the product (e.g., powder or cake) comprises the source of phosphate (e.g., potassium phosphate) at an amount less than about 50 wt %, optionally, less than about 40 wt %, less than about 30 wt %, or less than about 25 wt %. In some aspects, the product comprises about 15 wt % to about 25 wt % source of phosphate (e.g., potassium phosphate), optionally, about 17.87 wt % to about 21.85 wt %. In various aspects, the product comprises the source of chloride (e.g., sodium chloride) at an amount less than about 20 wt % or less than about 15 wt %. In some instances, the product comprises about 5 wt % to about 10 wt % source of chloride (e.g., sodium chloride), optionally, about 7.0 wt % to about 8.6 wt % sodium chloride. With regard to the presently disclosed powder, the recited wt % refers to the number of grams of the indicated component relative to the sum of the grams of all components of the powder excluding the live virus, and expressed as a percentage. For example, the wt % of rHSA=[(grams rHSA)÷(grams of rHSA+grams sugar+grams sugar alcohol+grams source of phosphate+grams source of chloride)]*100.

In exemplary instances, upon the addition of about 1 mL water (e.g., about 0.9 mL, about 1.0 mL, about 1.1 mL, or about 1.2 mL), the powder makes a liquid composition comprising about 80 mM to about 85 mM (e.g., about 80 mM, about 81 mM, about 82 mM, about 83 mM, about 84 mM, about 85 mM) potassium phosphate, about 95 mM to about 100 mM (e.g., about 95 mM, about 96 mM, about 97 mM, about 98 mM, about 99 mM, about 100 mM) sodium chloride, about 2.5% (w/v) to about 3.0% (w/v) (e.g., about 2.5% (w/v), about 2.6% (w/v), about 2.7% (w/v), about 2.8% (w/v), about 2.9% (w/v), about 3.0% (w/v)) sorbitol, about 0.35% (w/v) to about 0.40% (w/v) (e.g., about 0.35% (w/v), about 0.36% (w/v), about 0.37% (w/v), about 0.38% (w/v), about 0.39% (w/v), about 0.40% (w/v)) sucrose, and about 1.95% (w/v) to about 2.05% (w/v) (e.g., about 1.95% (w/v), about 1.96% (w/v), about 1.97% (w/v), about 1.98% (w/v), about 1.99% (w/v), about 2.00% (w/v), about 2.01% (w/v), about 2.02% (w/v), about 2.03% (w/v), about 2.04% (w/v), about 2.05% (w/v)) recombinant HSA. In other exemplary instances, sufficient water is added to reconstitute the powder to about 1 mL in volume.

A liquid composition comprising water and the presently disclosed dehydrated product or the presently disclosed powder or cake is provided herein. In some aspects, the liquid composition comprises about 0.95 mL to about 1.5 mL water, optionally, about 1.0 mL water. In certain aspects, the liquid composition comprises at least or about $10^6$ PFU live, attenuated virus per mL liquid composition, has a pH of about 7.4, and comprises about 80 mM to about 85 mM potassium phosphate, about 95 mM to about 100 mM sodium chloride, about 2.8% (w/v) to about 3.0% (w/v) sorbitol, about 0.36% (w/v) to about 0.40% (w/v) sucrose, and about 1.98% (w/v) to about 2.02% (w/v) recombinant HSA. In other aspects, the liquid composition comprises at least or about $10^8$ PFU live, attenuated virus per mL liquid composition, has a pH of about 7.4, and comprises about 80 mM to about 85 mM potassium phosphate, about 95 mM to about 100 mM sodium chloride, about 2.8% (w/v) to about 3.0% (w/v) sorbitol, about 0.36% (w/v) to about 0.40% (w/v) sucrose, and about 1.98% (w/v) to about 2.02% (w/v) recombinant HSA.

Methods of Preparing

The present disclosure also provides methods of preparing an oncolytic virus for administration to a human subject, comprising adding water to any one of the presently disclosed powders, optionally, wherein about 1.0 mL to about 1.2 mL water is added to the powder. Optionally, the prepared drug product is reconstituted not more than about 24, 36, or 48 hours prior to administration to the human subject.

Methods of Treatment

Further provided is a method of treating a subject with a tumor or a cancer. In exemplary embodiments, the method comprises administering to the subject a liquid composition of the present disclosure. In various instances, the method comprises adding water to any one of the presently disclosed dehydrated products (e.g., a lyophilized product, a freeze-dried product), which may be in the form of a powder or a cake, to obtain a liquid composition and administering the liquid composition to the subject. In exemplary instances, about 0.9 mL to about 1.2 mL water is added to the powder to obtain a liquid composition and the method comprises injecting the liquid composition into the human subject.

The presently disclosed compositions can be used to treat various tumors and cancers. For instance, a subject is treated for a solid tumor by the presently disclosed method. For example, the subject is treated for a cancer or tumor of the prostate, breast, lung, liver, bladder, kidney, cervix, or colon. In various aspects, the cancer or tumor is a renal cell cancer or tumor, an endometrial cancer or tumor, or is a cervical carcinoma; adenocarcinoma; melanoma; lymphoma; or glioma. In various aspects, the subject has a sarcoma such as soft tissue and bone sarcomas. The subject, in certain aspects, has cancer of the head and neck. In various aspects, the subject has a cancer, neoplasm or malignant tumor, e.g., leukemia, carcinoma, sarcoma. The cancer in some aspects is cancer of the breast, brain, cervix, colon, head & neck, liver, kidney, lung, non-small cell lung, melanoma, mesothelioma, ovary, sarcoma, stomach, uterus and Medulloblastoma. Also, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer. Such cancers and tumors are treated by the method of the present disclosures.

As used herein, the terms "patient" or "subject" are used interchangeably and mean a mammal, including, but not limited to, a human or non-human mammal, such as a bovine, equine, canine, ovine, or feline. Preferably, the patient is a human.

A method of killing tumor cells is additionally provided herein. In some aspects, the tumor cells are cells of an astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma or epidermoid carcinoma cells.

Combinations

The compositions, powders and lyophilized or freeze-dried products may be used in combination with other treatment modalities, including without limitation radiation, chemotherapy, thermotherapy, therapeutic proteins and surgery. The compositions, powders and lyophilized or freeze-dried products may be administered prior to, simultaneously with or following the other treatment modalities.

Therapeutic proteins include immune check point inhibitors. As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD1 with its ligands PDL1 and PDL2. These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. Check point inhibitors include cytotoxic T-lymphocyte associated antigen 4 (CTLA-4) inhibitors. Inhibitors of CTLA-4 include tremelimumab, ipilimumab (also known as 10D1, MDX-D010) and marketed under the name Yervoy™ and anti-CTLA-4 antibodies described in U.S. Pat. Nos. 5,811,097; 5,811,097; 5,855,887; 6,051,227; 6,207,157; 6,682,736; 6,984,720; and 7,605,238. Other immune checkpoint proteins includes programmed cell death 1 (PD-1) and programmed cell death ligands 1 and 2 (PDL1) (PDL2). Examples of molecules that inhibit PD1 and PDL1 and PDL2 include nivolumab (MDX 1106, BMS 936558, ONO 4538), a fully human IgG4 antibody that binds to and blocks the activation of PD-1 by its ligands PD-L1 and PD-L2; pembrolizumab (lambrolizumab, MK-3475 or SCH 900475) marketed as Keytruda™; MPDL3280A, an engineered anti-PDL1 antibody (atezolizumab); CT-011; AMP-224; BMS-936559 (MDX-1105-01 and those described in U.S. Pat. Nos. 7,488,802; 7,943,743; 8,008,449; 8,168,757; 8,217,149, and PCT Published Patent Application Nos: W003042402, WO2008156712, W02010089411, W02010036959, WO2011066342, WO2011159877, WO2011082400, and WO2011161699. Other immune-checkpoint inhibitors include lymphocyte activation gene-3 (LAG-3) inhibitors, such as IMP321, a soluble Ig fusion protein; B7 inhibitors, such as anti-B7-H3 antibody MGA271. Also included are TIM3 (T-cell immunoglobulin domain and mucin domain 3) inhibitors.

Physicians may administer the presently disclosed compositions, powders and lyophilized or freeze-dried products until a dosage is reached that achieves the desired effect. The compositions, powders and lyophilized or freeze-dried products may therefore be administered as a single dose, or as two or more doses (which may or may not contain the same amount of the desired molecule) over time, by direct injection or other suitable administration method. The compositions, powders and lyophilized or freeze-dried products of the present disclosure may be administered, for example, once or more than once, e.g., at regular intervals over a period of time. In general, the compositions, powders and lyophilized or freeze-dried products of the present disclosure may be administered until the patient manifests a medically relevant degree of improvement over baseline for the chosen indicator or indicators.

In one embodiment the compositions, powders and lyophilized or freeze-dried products comprise talimogene laherparepvec and is administered by intratumoral injection into injectable cutaneous, subcutaneous, and nodal tumors at a dose of up to 4.0 ml of $10^6$ plaque forming unit/mL (PFU/mL) at day 1 of week 1 followed by a dose of up to 4.0 ml of $10^8$ PFU/mL at day 1 of week 4, and every 2 weeks (±3 days) thereafter. The recommended volume of talimogene laherparepvec to be injected into the tumor(s) is dependent on the size of the tumor(s). All reasonably injectable lesions (cutaneous, subcutaneous and nodal disease that can be injected with or without ultrasound guidance) should be injected with the maximum dosing volume available on an individual dosing occasion. On each treatment day, prioritization of injections is recommended as follows: any new injectable tumor that has appeared since the last injection; by tumor size, beginning with the largest tumor; any previously uninjectable tumor(s) that is now injectable.

The following examples are given merely to illustrate the present invention and not in any way to limit its scope.

EXAMPLES

Example 1

This example describes exemplary compositions and products of the present disclosure.

A liquid composition comprising the components listed in Table 1 at the amounts indicated was made. The live virus (either $1 \times 10^6$ PFU or $1 \times 10^8$ PFU) was added to the mixture.

TABLE 1

| Component | Amount | Amount |
|---|---|---|
| Talimogene laherparepvec (amount of active virus after lyophilization and reconstitution) | $1 \times 10^6$ PFU or $1 \times 10^8$ PFU/mL | $1 \times 10^6$ PFU or $1 \times 10^8$ PFU/mL |
| Potassium phosphate | 14.5 (mg/mL) | 83 mM |
| Sodium chloride | 5.7 (mg/mL) | 98 mM |
| Sorbitol | 29.0 (mg/mL) | 159 mM |
| Sucrose | 3.8 (mg/mL) | 11 mM |
| Recombinant Human Serum Albumin | 20.0 (mg/mL) | 0.3 mM |
| Water for Injection (WFI) | Enough to reconstitute to ~1 mL | Enough to reconstitute to ~1 mL |
| Osmolality | 550 mOsm/kg | 550 mOsm/kg |
| pH | 7.4 | 7.4 |

The mixture was filled into glass vials and placed onto pre-cooled shelves in a freeze-dryer and dried according to the following parameters, which were developed to minimize potency loss and obtain a solid cake with acceptable residual moisture content and of acceptable visual appearance.

After freeze-drying, the resulting freeze-dried or lyophilized product is analyzed by plaque assay to determine viral potency as the primary indicator of recovery and stability performance. In addition, the product is also evaluated for cake appearance, protein content, particle content, and residual water content.

Example 2

This example describes a method of storing the freeze-dried or lyophilized product described in Example 1.

The freeze-dried or lyophilized product described in Example 1 (comprising either $1 \times 10^6$ or $1 \times 10^8$ PFU/mL virus) was stored at varying temperatures of 8° C. and below (e.g., 5° C., −20° C.) for a variety of storage times (e.g., up to 60 weeks). Another freeze-dried or lyophilized product was made as essentially described in Example 1, except that the amount of live virus was $1 \times 10^7$ PFU/mL. Aliquots of this product were also stored at varying temperatures of 8° C. and below (e.g., 5° C. and −20° C.) for a variety of storage times (e.g. up to 60 weeks).

After storage, an aliquot of each lyophilizate was reconstituted with about 1.0-1.2 mL water. The potency of the virus present in the reconstituted material was tested by a plaques assay, which is a standard cell culture method in virology that uses permissive cells in culture to quantitate the overall infectivity and replication performance of the virus.

Lyophilization of active biological compounds often results in a significant loss of activity, thus one of the goals in developing a lyophilized formulation is to minimize the extent of potency loss caused by lyophilization. As shown in Table 2, the formulation results in a potency loss of approximately 60% (or 0.4 $\log_{10}$ PFU/mL), for both the $1 \times 10^6$ PFU/mL and $1 \times 10^8$ PFU/mL virus concentrations, indicating the extent of loss is independent of the concentration of the active ingredient. The loss in potency represents a significant improvement compared to losses observed when traditional frozen formulations were lyophilized which can exhibit a loss of 1 $\log_{10}$ PFU/mL or greater (equivalent to 90% or greater loss).

TABLE 1

Summary of Potency loss due to lyophilization

| Target Strength (PFU/mL) | Potency Loss (%) due to Lyophilization) |
|---|---|
| $1 \times 10^6$ | 58 |
| $1 \times 10^8$ | 57 |

Table 3 contains potency data for the lyophilized virus targeted to contain $1 \times 10^6$ PFU/mL and stored at −20° C. and 5° C. for up to 60 weeks. Overall, there is no significant change in the potency of the lyophilized virus over 60 weeks at the indicated storage temperatures, indicating the material has been successfully stabilized. The deviations in potency are within the variability of the method.

TABLE 2

Potency of Lyophilized Virus Targeted to Contain 1 × $10^6$ PFU/mL Stored at −20° C. and 5° C.

| | Potency ($\log_{10}$ PFU/mL) | |
|---|---|---|
| Weeks | −20° C. | 5° C. |
| 0 | 5.9 | 5.9 |
| 9 | 6.1 | 5.5 |
| 30 | 5.9 | 5.7 |
| 60 | 6.0 | 5.8 |

Table 4 contains potency data for the lyophilized virus targeted to contain $1 \times 10^8$ PFU/mL and stored at 5° C. for up to 13 weeks. Overall, there is no significant change in the potency of the lyophilized virus over 13 weeks at the indicated storage temperatures, indicating the material has been successfully stabilized. The deviations in potency are within the variability of the method

TABLE 3

Potency of Lyophilized Virus Targeted to Contain
1 × 10$^8$ PFU/mL Stored at 5° C.

| Weeks | Potency (Log$_{10}$ PFU/mL) at 5 C. |
|---|---|
| 0 | 8.0 |
| 4 | 8.1 |
| 9 | 8.0 |
| 13 | 7.9 |

The reconstituted material was also tested for pH and osmolality with resulting values of pH 7.4 and an osmolality of 550 mOsm/kg.

Figure 2:
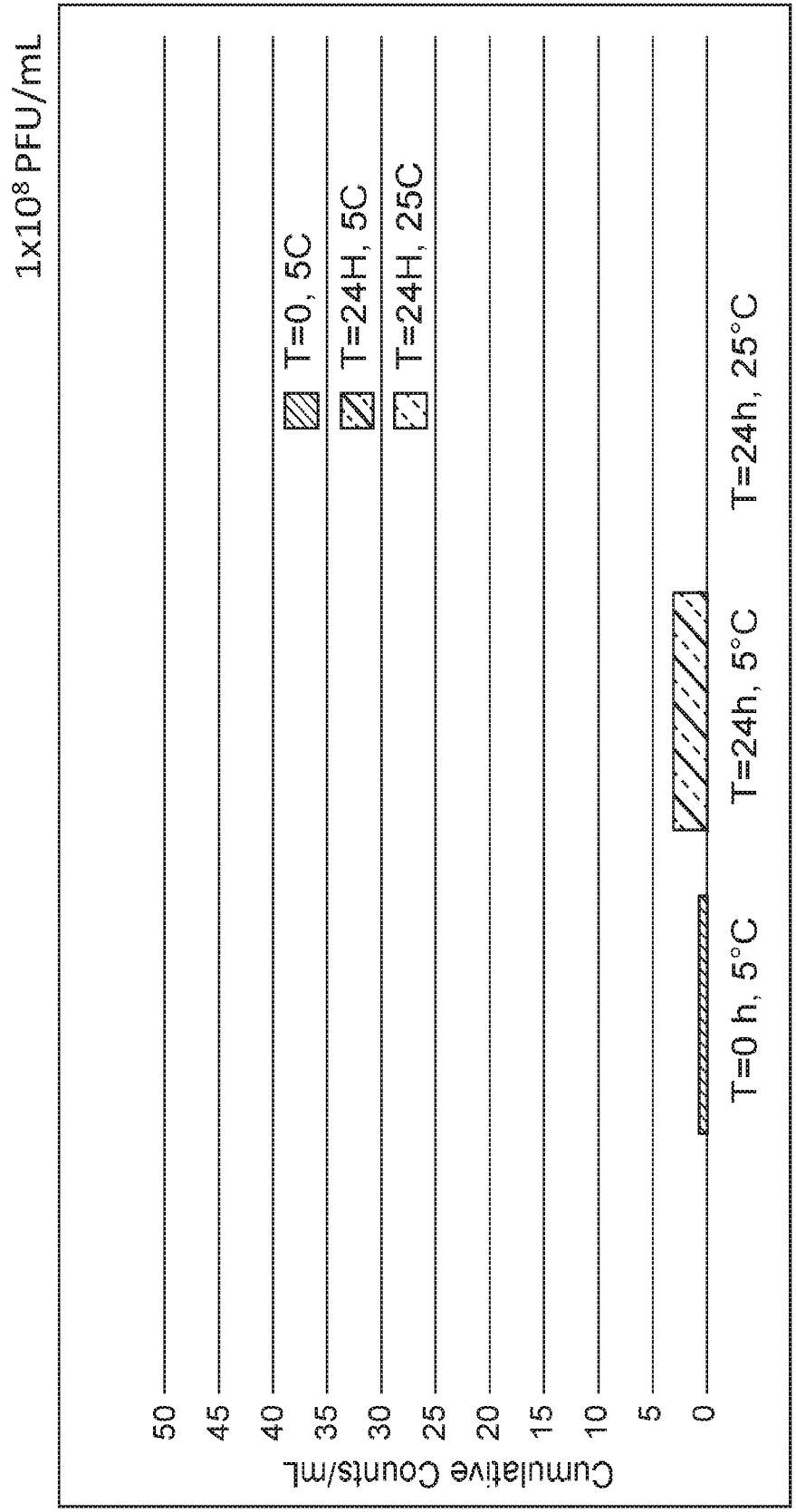
FIG. 2 is a graph of cumulative counts/mL depicting the quantity of subvisible particles >25 μm in reconstituted material formulated to contain 1×10$^8$ PFU/mL.

Product appearance is an important product attribute; a product which does not meet its specified appearance criteria could result in the rejection or recall of the relevant virus lot. The formation of particulates, either during manufacture or at later times (e.g., during storage), is a significant concern with all biologics. Due to the formulation, the reconstituted material (with 1×10$^6$ PFU/mL of virus) is virtually free of any visually detectable particles and as shown in FIGS. 1 and 2, also exhibits extremely low levels of subvisible particles. Similar results were obtained with material formulated to contain 1×10$^6$ PFU/mL.

Example 3

This example demonstrates improved recovery of activity (virus infectivity) and subsequent storage stability of both liquid and lyophilized live virus formulations using different combinations of sugar and protein stabilizers compared to other known, similar compositions.

Lyophilization is a process that removes water from samples. Lyophilization typically results in improved storage stability compared to storage in the liquid state. However, because lyophilization involves freezing and dehydration (by sublimation), it is also stressful process, particularly to biological agents such as enveloped viruses. While lyophilization can improve long-term stability, the process stress can also inactivate a significant portion of the agent of interest causing significant loss of potency. A satisfactory formulation will not only provide adequate liquid stability, and stability in the dried state, but will also minimize losses due to the lyophilization process.

It is a known challenge to develop formulations that stabilize labile agents (such as enveloped viruses) simultaneously in both liquid and lyophilized states, as the optimal compositions for each state are mutually exclusive and thus, typically not ideal for the other. Nevertheless, for a lyophilized product it is important that a formulation adequately supports the stability of the active agent in both the liquid and lyophilized states, because nearly all stages of a manufacturing process preceding lyophilization occur in the liquid state and, thus, activity of the active ingredient must be preserved up to the point of lyophilization. Similarly, after lyophilization, if the product is to be reconstituted (e.g., for use as a liquid product), liquid stability is important in order to ensure potency is maintained for an appropriate duration to support subsequent handling and storage. In addition, the lyophilization process itself can be destructive to biological agents, particularly enveloped viruses, which are sensitive to osmotic stress and cryo-concentration effects that can occur during the freezing stage of lyophilization, as well as the dehydration effects that occur during the drying stages of lyophilization. To date, developing formulations that adequately stabilize a labile agent, such as an enveloped virus, in both the liquid and lyophilized states, remains a significant challenge.

Sucrose Phosphate Glutamate Albumin (SPGA) and SPGA-based formulations are well-known formulations in the field of stabilizing live-agents, such as viruses. See, e.g., White et al., Vacccine 34(32): 3676-3683 (2016) and Yannarell et al., J Virol Methods 102(1-2): 15-25 (2002).

Formulations

This study compared a formulation of the present invention (F4) to two SPGA-based formulations (F1 and F2), as well as a third formulation (F3). The F4 formulation differed from the SPGA-based formulations (F1 and F2) in that, e.g., F4 lacked glutamate, had limited amounts of sucrose, had increased amounts of phosphate, and contained a sugar alcohol. Human albumin was present in all four formulations to demonstrate the effects observed were not due to this single component, but rather the collective effect of all the components present in the formulations. To determine whether there were differences between serum-derived and recombinant-derived human albumins, formulation F1 was prepared with serum-derived human albumin (HSA) and F2 was prepared with recombinant human albumin (rHA). Formulations F3 and F4 were also prepared with recombinant human albumin, to enable relative comparisons to F2. Each formulation contained the same amount of starting virus (talimogene laherparepvec). Table 5 describes the composition of the formulations tested (F1, F2, and F3) versus a composition of the present invention (F4, which is also described in Table 1).

TABLE 5

| Excipient | F1 (SPGA + HSA) | F2 (SPGA + rHA) | F3 (P.rHA.S + rHA) | F4 (Lyo form. + rHA) |
|---|---|---|---|---|
| KPO4 | 11 mM | 11 mM | 1.2 mM | 83 mM |
| NaPO4 | | | 6.4 mM | |
| KCl | | | 2.2 mM | |
| NaCl | | | 110 mM | 98 mM |
| K-Glutamate | 4.5 mM | 4.5 mM | | |
| Na-Glutamate | | | 5.9 mM | |
| Sorbitol | | | | 2.9% |
| Sucrose | 7.5% | 7.5% | 5.0% | 0.4% |
| Human albumin (serum) | 1.0% | | | |
| Human albumin (recombinant) | | 1.0% | 1.0% | 1.0% |

The performance of the formulations described in Table 5 was evaluated by comparing the relative levels of viral infectivity, over time, in both the liquid and lyophilized states at different temperatures.

Liquid State Stability of Formulations

Figure 3:
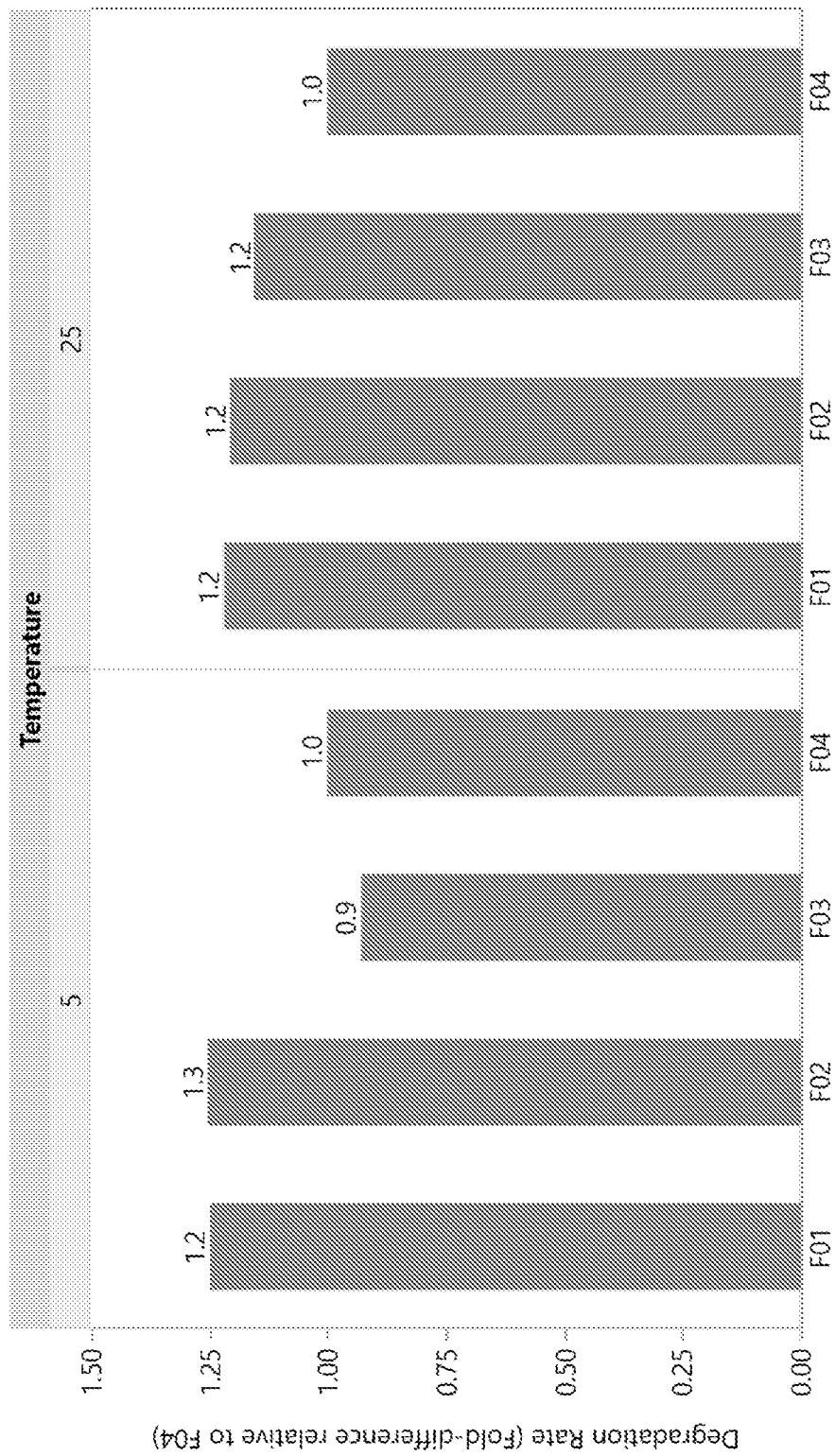
FIG. 3 is a comparison of degradation rates of formulations F1, F2, and F3 (each containing talimogene laherparepvec) relative to F4 (also containing talimogene laherparepvec) stored as a liquid at 5° C. (left half of FIG. 3) and 25° C. (right half of FIG. 3) for 6 weeks. Values greater than 1 indicate increased degradation rates relative to F4 (worse stability) and values less than 1 indicate extent of improved degradation rate (better stability) relative to F4.

Each of the four formulations (F1, F2, F3, F4) was prepared with equal amounts of talimogene laherparepvec and aliquots of each were stored at 5° C. and 25° C. and tested over time (for 9 weeks) by plaque assay to evaluate the amount of virus activity preserved (FIG. 3). FIG. 3 shows degradation rates relative to formulation F4. These were obtained by determining the degradation rate for each formulation and then normalizing the rate against the rate observed for formulation F4.

As can been seen from FIG. 3, at 5° C., formulations F1 and F2 degraded 1.2 and 1.3 times faster (worse) than F4, respectively, whereas formulation F3, performed slightly better than F4, degrading at a rate 0.9 times that of F4. At 25° C., a controlled-temperature indicative of room-temperature conditions, formulation F4 performed better than the other three formulations.

Overall, formulation F4 performed comparatively better than the other formulations. This is especially evident at the 25° C. condition which is a particularly relevant temperature from a manufacturing perspective.

Lyophilized State Stability of Formulations

F1, F2, F3, and F4 were filled into vials and lyophilized and tested over time by plaque assay to evaluate the amount of virus activity preserved as described in above section for Liquid State Stability of Formulations. After lyophilization, samples were either tested immediately after reconstitution to determine the amount of activity remaining after lyophilization, or were placed at 5° C. for 10 weeks to determine their storage stability performance. All four formulations were lyophilized together using a conservative lyophilization cycle, based on the lowest glass transition temperature of the formulations and the observation that all four formulations exhibit similar temperature-dependent profiles during lyophilization. Since each formulation was dried in a comparable and optimal manner, direct comparison of stability and of activity loss due to lyophilization (or activity recovery) can be made.

Figure 4:
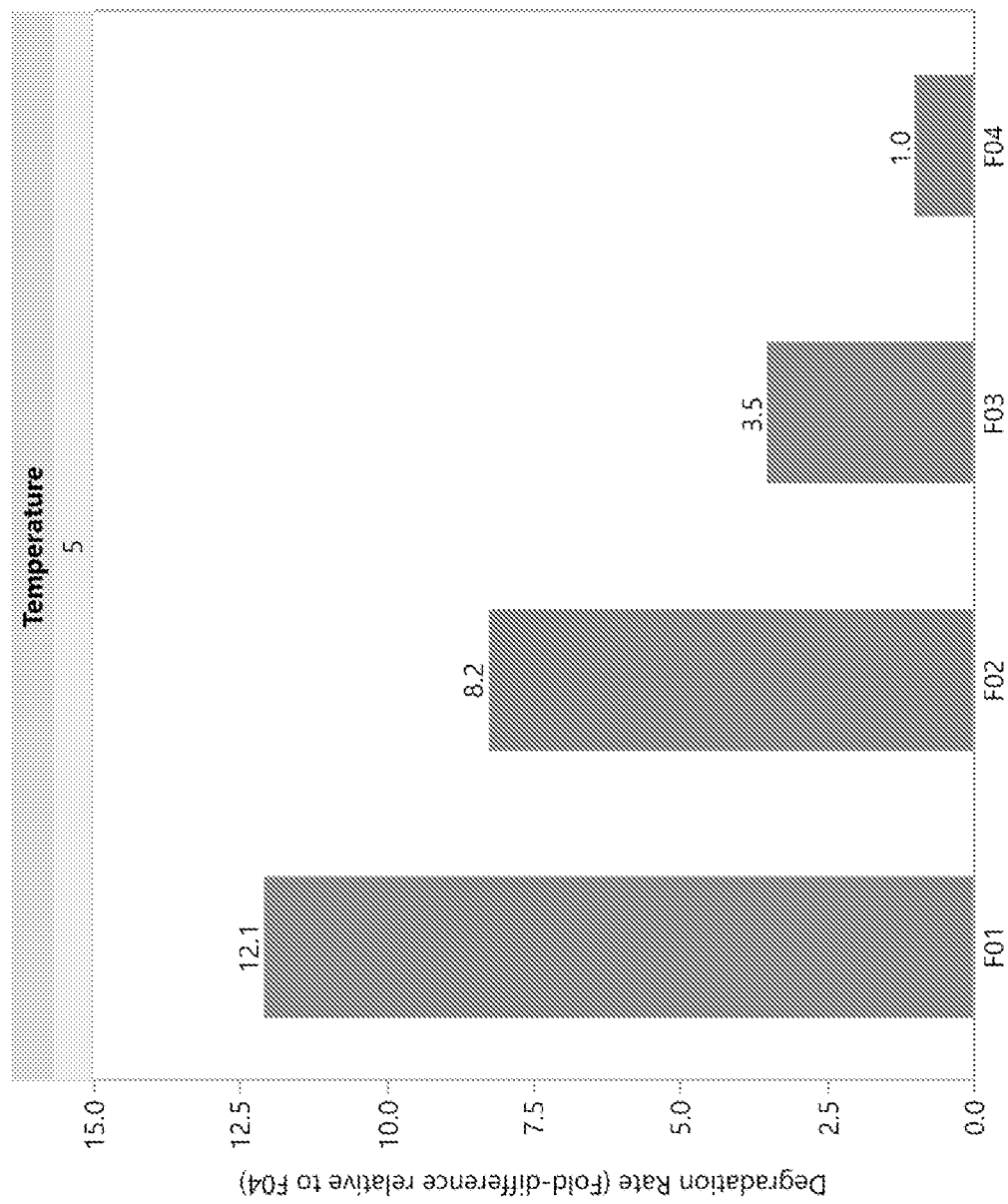
FIG. 4 is a comparison of degradation rates of lyophilized formulations of F1, F2, and F3 stored at 5° C. for 10 weeks, relative to F4. Values greater than 1 indicate fold-increase in degradation rate relative to F4 (i.e. worse stability) and values less than 1 (not present) would have indicated the fold-decrease in degradation rate (i.e. better stability) relative to F4.

A comparison of the stability of lyophilized talimogene laherparepvec in each of the formulations relative to formulation F4 is shown in FIG. 4. As can be seen, F4 is significantly more stable than F1 and F2, which degraded at rates 12.1 and 8.2 times faster than F4, respectively. Interestingly, F3, which performed slightly better than F4 in the liquid state, degraded 3.5 times faster in the lyophilized state.

Activity Recovery

In addition to stability during storage, another critical parameter for a lyophilized product is the amount of activity recovered after lyophilization (also referred to by its inverse condition, activity loss due to lyophilization).

Figure 5:
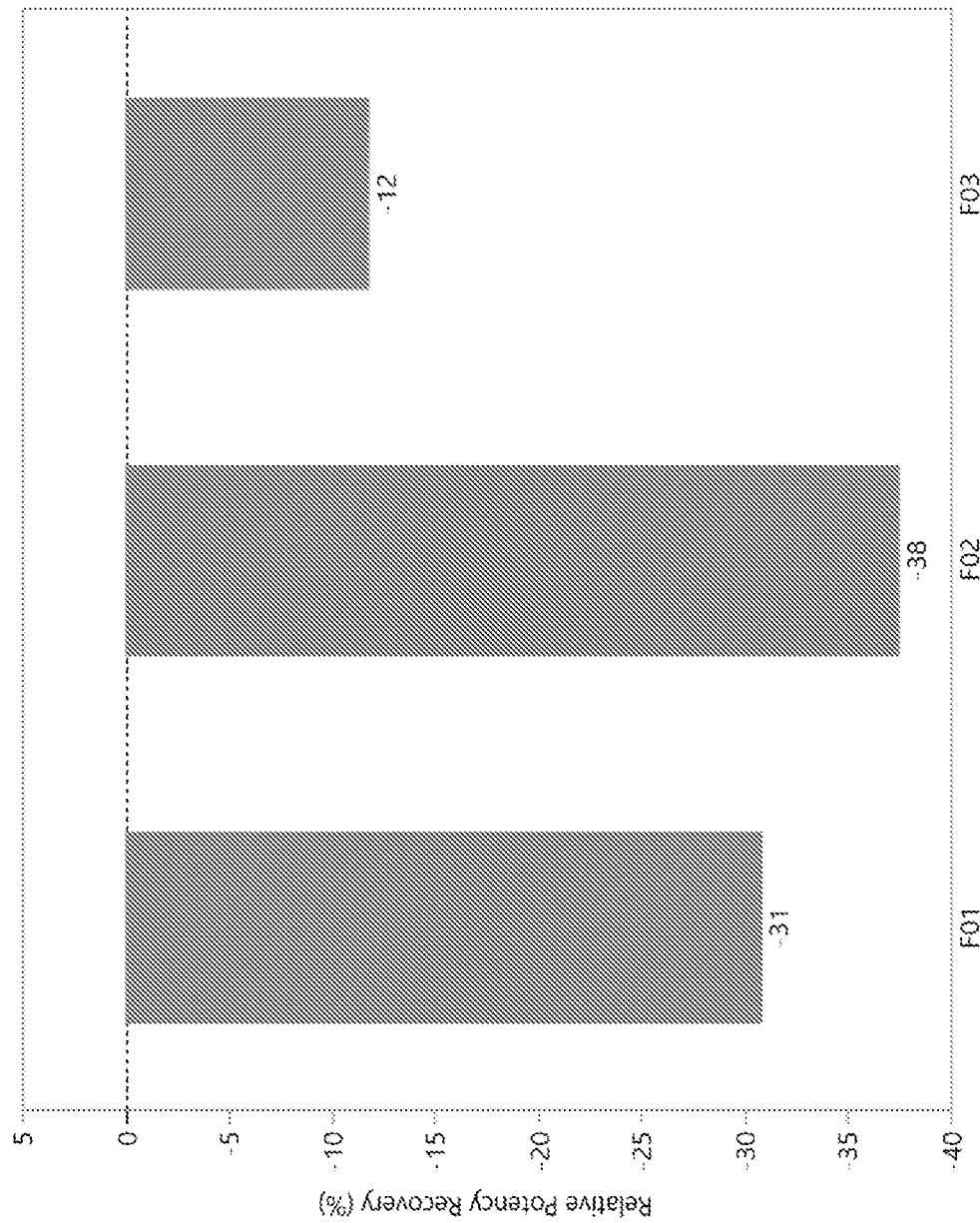
FIG. 5 demonstrates the recovery of activity after lyophilization of F1, F2, and F3 relative to formulation F4. The amount of activity recovered after lyophilization was calculated for each formulation by dividing the amount of activity initially present after lyophilization by the amount of amount activity present in the liquid formulation (pre-lyophilization) and then normalized to the fraction of activity recovered in formulation F4. Values greater than 0% (not present) would indicate the proportion of activity recovered greater than (i.e. better) than the amount of activity recovered with formulation F4. Values less than 0% indicate the proportion of activity recovered that was less than (i.e. worse) than the amount of activity recovered with formulation F4.

FIG. 5 shows the amounts of activity recovery relative to formulation F4. Activity recovery is calculated by determining the virus titer for each formulation before and after lyophilization. The titer before lyophilization represents 100% activity; the titer determined after lyophilization was used to calculate the percentage recovered. The recoveries were then normalized to formulation F4 to show how each formulation performed relative to F4 (F4 is not shown as it is set to 0%). It can be seen that Formulations F1 and F2 lost significantly more activity (viral titer) 31% and 38%, respectively, than F4. Additionally, F3 lost 12% more activity than F4. Overall these data indicate that F4 preserved more activity than F1, F2, and F3.

CONCLUSION

Overall, the Liquid State Stability, Lyophilized State Stability, and Activity Recovery data reveal that there are significant changes in performance between formulations F1, F2, F3, and F4. These data support that F4 preserved more activity after lyophilization, was significantly more stable and performed comparatively better, especially at the 25° C. condition, relative to formulations F1-F3.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A liquid composition comprising:
   a live, attenuated herpes simplex virus 1 (HSV-1);
   17.5 mg/mL to 22.5 mg/mL recombinant human serum albumin (rHSA);
   less than 5 mg/mL sucrose;
   26 mg/mL to 32 mg/mL sorbitol;
   13.5 mg/mL to 16 mg/mL potassium phosphate; and
   3 mg/mL to 7 mg/mL sodium chloride,
   wherein the composition is substantially free of lactose, gelatin, antibiotic, and free amino acids.

2. The liquid composition of claim 1, comprising 20 mg/mL±2 mg/mL rHSA.

3. The liquid composition of claim 1, comprising 3.8 mg/mL±0.38 mg/mL sucrose.

4. The liquid composition of claim 1, comprising 29 mg/mL sorbitol.

5. The liquid composition of claim 1, comprising 14.5 mg/mL potassium phosphate.

6. The liquid composition of claim 1, comprising 5.7 mg/mL sodium chloride.

7. The liquid composition of claim 1, wherein the pH of the liquid composition is 7.2 to 7.6.

8. The liquid composition of claim 7, wherein the pH of the liquid composition is 7.4.

9. The liquid composition of claim 1, wherein the osmolality of the liquid composition is less than 700 mOsm/kg.

10. The liquid composition of claim 9, wherein the osmolality of the liquid composition is 525 mOsm/kg to 575 mOsm/kg.

11. The liquid composition of claim 1, comprising not more than 0.01 mM of any of lactose, gelatin, antibiotic, and free amino acids.

12. The liquid composition of claim 1, wherein the HSV-1 is JS1, strain 17+, strain F, or strain KOS.

13. The liquid composition of claim 1, wherein the HSV-1 is talimogene laherparepvec, G207, OrienX010, NV1020, M032, ImmunoVEX or OncoVEX$^{GALV/CD}$.

14. The liquid composition of claim 1, wherein the HSV-1 comprises a functional deletion of both the ICP34.5 gene and the ICP47 gene.

15. The liquid composition of claim 13, wherein the HSV-1 is talimogene laherparepvec.

16. The liquid composition of claim 1, wherein the HSV-1 is RP-1, RP-2, or RP-3.

17. The liquid composition of claim 1, wherein said liquid composition comprises;
talimogene laherparepvec,
20 mg/mL rHSA;
3.8 mg/mL sucrose;
29 mg/mL sorbitol;
14.5 mg/mL potassium phosphate; and
5.7 mg/mL sodium chloride,
wherein the pH of the liquid composition is 7.4.

18. The liquid composition of claim 1, wherein upon lyophilization and reconstitution with water, the potency of the live, attenuated HSV-1 in the reconstituted product is at least 30% of the potency of the live, attenuated HSV-1 before the liquid composition is lyophilized.

19. A liquid composition consisting essentially of:
a live, attenuated HSV-1;
17.5 mg/mL to 22.5 mg/mL rHSA;
less than 5 mg/mL sucrose;
26 mg/mL to 32 mg/mL sorbitol;
13.5 mg/mL to 16 mg/mL potassium phosphate; and
3 mg/mL to 7 mg/mL sodium chloride.

20. The liquid composition of claim 19, wherein the HSV-1 is talimogene laherparepvec.

* * * * *